(12) United States Patent
Filla et al.

(10) Patent No.: US 6,358,972 B1
(45) Date of Patent: Mar. 19, 2002

(54) 5-HT$_{1F}$ AGONISTS

(75) Inventors: Sandra Ann Filla, Franklin; Daniel James Koch, Indianapolis; Brian Michael Mathes, Indianapolis; Vincent Patrick Rocco, Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/701,934

(22) PCT Filed: Jun. 25, 1999

(86) PCT No.: PCT/US99/14400

§ 371 Date: Dec. 5, 2000

§ 102(e) Date: Dec. 5, 2000

(87) PCT Pub. No.: WO00/00487

PCT Pub. Date: Jan. 6, 2000

Related U.S. Application Data

(60) Provisional application No. 60/091,198, filed on Jun. 30, 1998.

(51) Int. Cl.⁷ ..................... A61K 31/435; C07D 471/04
(52) U.S. Cl. ........................................ 514/300; 546/113
(58) Field of Search ........................... 546/113; 514/300

(56) References Cited

FOREIGN PATENT DOCUMENTS

| EP | 0 438 230 | 1/1991 |
|---|---|---|
| EP | 0 494 774 | 1/1992 |
| WO | WO 92/13856 | 2/1992 |
| WO | WO 94/14771 | 12/1993 |
| WO | WO 95/28400 | 4/1995 |

OTHER PUBLICATIONS

Agarwal, A. et al., Three–dimensional quantitative structure–activity relationships of 5–HT receptor binding data for tetrahydropyridinylindole derivatives: A comparison of the Hansch and Comfa methods, *Journal of medicinal Chemistry*, vol. 36, No. 25, pp. 4006–4014, XP000572300.

*Primary Examiner*—Bernard Dentz
(74) *Attorney, Agent, or Firm*—R. Craig Tucker; Robert D. Titus

(57) ABSTRACT

The present invention relates to a compound of formula (I): or a pharmaceutical acid addition salt thereof; which is useful for activating 5-HT$_{1f}$ receptors and inhibiting protein extravasation in a mammal.

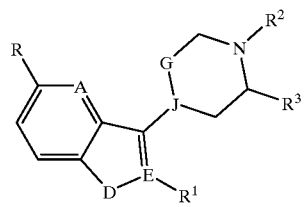

11 Claims, No Drawings

5-HT$_{1F}$ AGONISTS

This application is a 371 of PCT/US99/14400 filed Jun. 6, 1999 which is a continuation of Verified Provisional Application 60/091,198 filed Jun. 6, 1998.

Theories regarding the pathophysiology of migraine have been dominated since 1938 by the work of Graham and Wolff. *Arch. Neurol. Psychiatry*, 39:737–63, 1938. They proposed that the cause of migraine headache was vasodilatation of extracranial vessels. This view was supported by knowledge that ergot alkaloids and sumatriptan, a hydrophilic 5-HT$_1$ agonist which does not cross the blood-brain barrier, contract cephalic vascular smooth muscle and are effective in the treatment of migraine. Humphrey, et al., *Ann. NY Acad. Sci.*, 600:587–600, 1990. Recent work by Moskowitz has shown, however, that the occurrence of migraine headaches is independent of changes in vessel diameter. *Cephalalgia*, 12:5–7, 1992.

Moskowitz has proposed that currently unknown triggers for pain stimulate trigeminal ganglia which innervate vasculature within the cephalic tissue, giving rise to release of vasoactive neuropeptides from axons on the vasculature. These released neuropeptides then activate a series of events, a consequence of which is pain. This neurogenic inflammation is blocked by sumatriptan and ergot alkaloids by mechanisms involving 5-HT receptors, believed to be closely related to the 5-HT$_{1D}$ subtype, located on the trigeminovascular fibers. *Neurology*, 43(suppl. 3):S16–S20 1993.

Serotonin (5-HT) exhibits diverse physiological activity mediated by at least seven receptor classes, the most heterogeneous of which appears to be 5-HT$_1$. A human gene which expresses one of these 5-HT$_1$ receptor subtypes, named 5-HT$_{1F}$, was isolated by Kao and coworkers. *Proc. Natl. Acad. Sci. USA*, 90:408–412, 1993. This 5-HT$_{1F}$ receptor exhibits a pharmacological profile distinct from any serotonergic receptor yet described. The high affinity of sumatriptan at this subtype, K$_i$=23 nM, suggests a role of the 5-HT$_{1F}$ receptor in migraine.

This invention relates to novel 5-HT$_{1F}$ against which inhibit peptide extravasation due to stimulation of the trigeminal ganglia, and are therefore useful for the treatment of migraine and associated disorders.

The present invention relates to a compound of formula I:

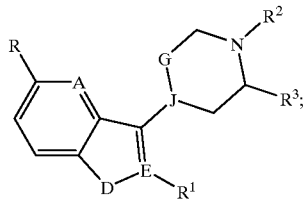

or a pharmaceutical acid addition salt thereof; where:
A is nitrogen or carbon;
D is oxygen, sulfur, or NH;
E is carbon or nitrogen;
G—J is CH$_2$—CH or CH=C;
R is phenyl, substituted phenyl, naphthyl, substituted naphthyl, heteroaryl, or substituted heteroaryl;
R$^1$ is hydrogen or C$_1$–C$_6$ alkyl;
R$^2$ is hydrogen or C$_1$–C$_6$ alkyl;
R$^3$ is hydrogen or R$^2$ and R$^3$ combine, together with the 6 membered ring to which they are attached, to form a 6:5, 6:6, or 6:7 fused bicyclic ring; with the proviso that 1) A may be nitrogen only when D is NH and E is carbon;
2) E may be nitrogen only when D is NH and A is carbon;
3) when E is nitrogen, R$^1$ is not a substituent; or a pharmaceutical acid addition salt thereof.

This invention also relates to a pharmaceutical formulation comprising a compound of formula I, or a pharmaceutical acid addition salt thereof, and a pharmaceutical carrier, diluent, or excipient.

In addition, the present invention relates to a method for activating 5-HT$_{1F}$ receptors in mammals comprising administering to a mammal in need of such activation an effective amount of a compound of formula I, or a pharmaceutical acid addition salt thereof.

Moreover, the current invention relates to a method for inhibiting neuronal protein extravasation comprising administering to a mammal in need of such inhibition an effective amount of a compound of formula I, or a pharmaceutical acid addition salt thereof.

One embodiment of this invention is a method for increasing activation of the 5-HT$_{1F}$ receptor for treating a variety of disorders which have been linked to decreased neurotransmission of serotonin in mammals. Included among these disorders are depression, migraine pain, bulimia, premenstrual syndrome or late luteal phase syndrome, alcoholism, tobacco abuse, panic disorder, anxiety, general pain, post-traumatic syndrome, memory loss, dementia of aging, social phobia, attention deficit hyperactivity disorder, disruptive behavior disorders, impulse control disorders, borderline personality disorder, obsessive compulsive disorder, chronic fatigue syndrome, premature ejaculation, erectile difficulty, anorexia nervosa, disorders of sleep, autism, mutism, trichotillomania, trigeminal neuralgia, dental pain or temperomandibular joint dysfunction pain. The compounds of this invention are also useful as a prophylactic treatment for migraine. Any of these methods employ a compound of formula I.

The use of a compound of formula I for the activation of the 5-HT$_{1F}$ receptor, for the inhibition of peptide extravasation in general or due to stimulation of the trigeminal ganglia specifically, and for the treatment of any of the disorders described above, are all embodiments of the present invention.

The general chemical terms used throughout have their usual meanings. For example, the term "6:5, 6:6, or 6:7 fused bicyclic ring" refers to moieties of the formula:

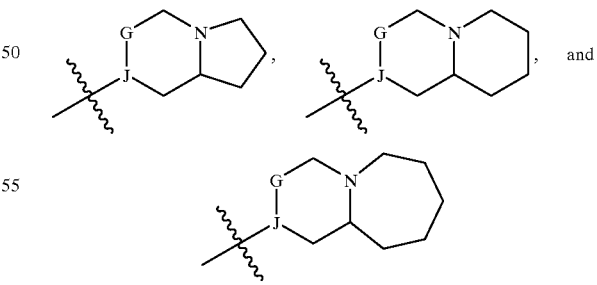

respectively.

The compounds of formula I where R$^2$ and R$^3$ combine, together with the 6 membered ring to which they are attached, to form a 6:5, 6:6, or 6:7 fused bicyclic ring (indolizinyl, quinolizinyl, or 1-azabicyclo[5.4.0]undecanyl ring respectively) contain a chiral center located in that bicyclic ring. This chiral center is located at the bridgehead carbon ring system. Furthermore, when R² and R³ combine and G—J is CH₂—CH, the CH group of G—J is a chiral center as well. Such centers are designated "R" or "S". For the purposes of the present application, the numbering system for naming the substituents around the 1H-indole, benzofuran, benzothiophene, indazole, and 4-aza-1H-indole rings and the R,R and S,S enantiomers are illustrated below where n is 0, 1, or 2 and A, D, E, R, and R¹ are as defined above.

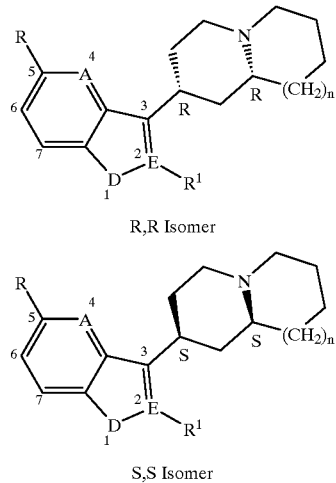

R,R Isomer

S,S Isomer

All enantiomers (S,R; R,S; S,S; R,R), diastereomers, and mixtures thereof, are included within the scope of the present invention.

The term "C₁–C₄ alkyl" includes such groups as methyl, ethyl, n-propyl, isopropyl, cyclopropyl, n-butyl, isobutyl, sec-butyl, tert-butyl, and cyclobutyl. The term "C₁–C₆ alkyl" includes those groups listed for C₁–C₄ alkyl and also refers to saturated straight, branched, or cyclic hydrocarbon chains of 5 to 6 carbon atoms. Such groups include, but are not limited to, pentyl, pent-2-yl, pent-3-yl, neopentyl, cyclopentyl, hexyl, cyclohexyl, and the like.

The term "halo" includes fluoro, chloro, bromo and iodo.

The term "C₁–C₆ alkoxy" refers to a C₁–C₆ alkyl group bonded through an oxygen atom. The term "C₁–C₄ alkoxy" refers to a C₁–C₄ alkyl group bonded through an oxygen atom. The term "C₁–C₄ alkylthio" refers to a C₁–C₄ alkyl group bonded through a sulfur atom. The term "(C₁–C₄ alkyl)sulfonyl" refers to a C₁–C₄ alkyl group bonded through a sulfonyl moiety. The term "C₁–C₄ acyl" refers to a formyl group or a C₁–C₃ alkyl group bonded through a carbonyl moiety.

The terms "substituted phenyl" and "substituted naphthyl" refer to a phenyl and naphthyl moiety, respectively, substituted once with halo, C₁–C₄ alkyl, C₁–C₆ alkoxy, C₁–C₄ alkylthio, nitro, cyano, amino, (C₁–C₄ alkyl)₂amino, NH—(C₁–C₄ acyl), NHC(O)-heteroaryl, NHC(O)-phenyl, NHC(O)-substituted phenyl, carboxamido, trifluoromethyl, trifluoromethoxy, phenyl, C₁–C₄ acyl, benzoyl or (C₁–C₄ alkyl)sulfonyl, or two to three substituents independently selected from: halo, nitro, C₁–C₄ alkyl, trifluoromethyl, and C₁–C₄ alkoxy.

The term "heteroaryl" is taken to mean an aromatic 5- or 6-membered ring containing from 1 to 3 heteroatoms selected from: nitrogen, oxygen and sulfur, said ring optionally being benzofused. Aromatic rings include furyl, thienyl, pyridinyl, pyrrolyl, N-methylpyrrolyl, oxazolyl, isoxazolyl, pyrazolyl, imidazolyl, triazolyl, oxadiazolyl, thiadiazolyl, thiazolyl, pyrimidinyl, pyrazinyl, pyridazinyl, and the like. Benzofused aromatic rings include isoquinolinyl, benzoxazolyl, benzthiazolyl, quinolinyl, benzofuranyl, benzothiophenyl, indolyl and the like.

The term "substituted heteroaryl" is taken to mean an aromatic or benzofused aromatic heterocycle as defined in the previous paragraph substituted with up to three substituents independently selected from: halo, C₁–C₄ alkoxy, C₁–C₄ alkyl, cyano, nitro, hydroxy, NHC(O)-heteroaryl, S(O)ₙ—(C₁–C₄ alkyl) and S(O)ₙ-phenyl where n is 0, 1, or 2.

The term "amino protecting group" as used in this specification refers to a substituents commonly employed to block or protect the amino functionality while reacting other functional groups on the compound. Examples of such amino-protecting groups include the formyl group, the trityl group, the triisopropyl silyl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like; and like amino protecting groups. The species of amino protecting group employed is not critical so long as the derivitized amino group is stable to the condition of subsequent reactions on other positions of the molecule and can be removed at the appropriate point without disrupting the remainder of the molecule. Further examples of groups referred to by the above terms are described by T. W. Greene, "Protective Groups in Organic Synthesis", John Wiley and Sons, New York, N.Y., 1991, Chapter 7 hereafter referred to as "Greene".

The term "pharmaceutical" when used herein as an adjective, means substantially non-toxic and substantially non-deleterious to the recipient.

By "pharmaceutical formulation" it is further meant that the carrier, solvent, excipients and salt must be compatible with the active ingredient of the formulation (a compound of formula I).

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D. C., *J. Pharm. Sci.*, 66:1, 1977.

The term "effective amount" means an amount of a compound of formula I which is capable of activating 5-HT₁F receptors and/or inhibiting neuronal protein extravasation.

The term "suitable solvent" refers to any solvent, or mixture of solvents, inert to the ongoing reaction that sufficiently solubilizes the reactants to afford a medium within which to effect the desired reaction.

The following group is illustrative of compounds contemplated within the scope of this invention:

5-phenyl-3-(1-methylpiperidin-4-yl)benzofuran;

5-(4-fluorophenyl)-3-(octahydroindolizin-7-yl)-2-methylbenzothiophene;

5-(2-chlorophenyl)-2-chloroethenyl)-3-(1-ethylpiperidin-4-yl)-2-ethyl-1H-indole;

5-(3-methoxyphenyl)-3-(octahydro-2H-quinolizin-2-yl)-1H-indazole;

5-(3,4,5-trifluorophenyl)-3-(1-propylpiperidin-4-yl)-2-propyl-4-aza-1H-indole;

5-(thien-2-yl)-3-(1-azabicyclo[5.4.0]undecan-4-yl)-2-cyclopropylbenzofuran;

5-(thien-3-yl)-3-(1-isopropylpiperidin-4-yl)-2-n-butylbenzothiophene;

5-(benzamidazol-2-yl)-3-(octahydroindolizin-7-yl)-2-s-butyl-1H-indole;
5-(naphth-1-yl)-3-(1-n-butylpiperidin-4-yl)1H-indazole;
5-(pyrazin-2-yl)-3-(octahydro-2H-quinolizin-2-yl)-2-t-butyl-4-aza-1H-indole;
5-(oxazol-2-yl)-3-(1-s-butylpiperidin-4-yl)-2-cyclobutylbenzofuran;
5-(quinolin-4-yl)-3-(1-azabicyclo[5.4.0]undecan-4-yl)benzothiophene;
5-(isothiazol-5-yl)-3-(1-t-butylpiperidin-4-yl)1H-indole;
5-(pyrimidin-2-yl)-3-(octahydroindolizin-7-yl)1H-indazole;
5-(isoxazol-4-yl)-3-(1-cyclopropylpiperidin-4-yl)4-aza-1H-indole;
5-(benzimidazol-2-yl)-3-(octahydro-2H-quinolizin-2-yl)benzofuran;
5-(5-fluorobenzimidazol-2-yl)-3-(1-cyclobutylpiperidin-4-yl)benzothiophene;
5-(5-methoxybenzimidazol-2-yl)-3-(1-azabicyclo[5.4.0]undecan-4-yl)1H-indole;
5-(naphth-2-yl)-3-(1-methylpiperidin-4-yl)1H-indazole;
5-(5-fluoronaphth-2-yl)-3-(octahydroindolizin-7-yl)4-aza-1H-indole;
5-(7-methoxynaphth-1-yl)-3-(1-methylpiperidin-4-yl)-2-methylbenzofuran;
5-(3-chloronaphth-1-yl)-3-(1,2,3,4,5,8-hexahydroindolizin-7-yl)-2-ethyl benzothiophene;
5-(4-trifluoromethylnaphth-2-yl)-3-(1-ethylpiperidin-4-yl)-2-propyl-1H-indole;
5-(3,5-difluoro-4-methoxyphenyl)-3-(1,4,5,6,7,8,9-heptahydroquinolizin-2-yl)-1H-indazole;
5-(2-carboxamidonaphth-1-yl)-3-(1-propylpiperidin-4-yl)-2-cyclopropyl-4-aza-1H-indole; and
5-(thiazol-2-yl)-3-(1-azabicyclo[5.4.0]undec-3-en-4-yl)-2-isopropylbenzofuran.

While all enantiomers, all diastereomers, and mixtures thereof are useful as 5-HT$_{1F}$ agonists, single enantiomers and single diastereomers are preferred. Furthermore, while all of the compounds of this invention are useful as 5-HT$_{1F}$ agonists, certain classes are preferred. The following paragraphs describe such preferred classes.

a) A is carbon;
b) A is nitrogen, D is NH, and E is carbon;
c) D is NH and E is carbon;
d) D is sulfur;
e) D is oxygen;
f) D is NH and E is nitrogen;
g) G—J is CH$_2$—CH;
h) G—J is CH=C;
i) R$^1$ is hydrogen;
j) R$^1$ is C$_1$–C$_4$ alkyl;
k) R$^1$ is methyl;
l) R$^2$ is hydrogen or C$_1$–C$_4$ alkyl;
m) R$^2$ is methyl;
n) R$^2$ and R$^3$ combine, together with the 6 membered ring to which they are attached, to form a 6:5, 6:6, or 6:7 fused bicyclic ring;
o) R$^2$ and R$^3$ combine, together with the 6 membered ring to which they are attached, to form a 6:6 fused bicyclic ring;
p) when R$^2$ and R$^3$ combine, together with the 6 membered ring to which they are attached, to form a 6:5, 6:6, or 6:7 fused bicyclic ring, the compound is the R,R or S,R isomer;
q) when R$^2$ and R$^3$ combine, together with the 6 membered ring to which they are attached, to form a 6:5, 6:6, or 6:7 fused bicyclic ring, the compound is the S,S or R,S isomer;
r) the substitution patterns found in the compounds of the Examples section;
s) the compounds of the Examples section;
t) the compound is an acid addition salt;
u) the compound is the hydrochloride salt;
v) the compound is the oxalate salt; and
w) the compound is the fumarate salt.

It will be understood that the above classes may be combined to form additional preferred classes.

It is preferred that the mammal to be treated by the administration of compounds of this invention is human.

The compounds of formula I may be prepared via a catalytic biaryl cross-coupling reaction. For a review of these cross coupling reactions see, e.g., Stanforth, S. P., "Catalytic Cross-coupling Reactions in Biaryl Synthesis", Tetrahedron, 54:263–303, 1998. Typically, compounds of formula I may be prepared from compounds of formula II and III as illustrated in Scheme 1 below where R$^4$ and R$^5$ are chloro, bromo, OSO$_2$CF$_3$, B(OH)$_2$, or Sn(C$_1$–C$_4$ alkyl)$_3$ provided that one of R$^4$ and R$^5$ must be selected from chloro, bromo, and OSO$_2$CF$_3$ and one of R$^4$ or R$^5$ must be selected from B(OH)$_2$ and Sn(C$_1$–C$_4$ alkyl)$_3$ and A, D, E, G, J, R$^2$, and R$^3$ are as defined above.

Scheme 1

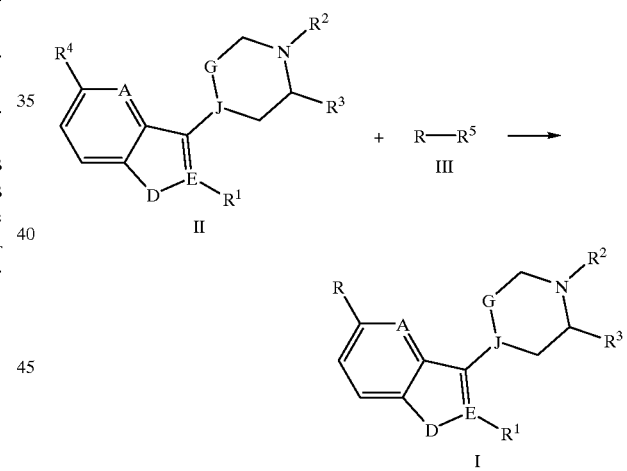

Compounds of formula I may be prepared by various aryl-aryl coupling methods. One such method is the Suzuki coupling, i.e., the coupling of an aryl halide or triflate with an aryl boronic acid. For a review of the Suzuki coupling, see, e.g., Tetrahedron, 54:285–292, 1998. Such a coupling may be performed by dissolving or suspending an aryl boronic acid of formula II or III, an aryl chloride, bromide, or triflate of formula II or III, a catalytic amount of palladium(0), and a weak aqueous base in a suitable solvent such as tetrahydrofuran or toluene. Typical reaction temperatures range from ambient to the reflux temperature of the mixture. Preferably, the reaction is performed at the reflux temperature of the mixture. Typical reaction times range from 1 to about 48 hours but, generally, the reaction is substantially complete after about 18 hours.

Generally, the aryl boronic acid is employed in a molar excess relative to the aryl halide. Such excesses typically range from about 1.01 to about 1.6 equivalents. Suitable sources of palladium(0) include, but are not limited to, palladium(0) bis(dibenzylidineacetone), tetrakis (triphenylphosphine)palladium(0), [bis(diphenylphosphino) ferrocene]dichloropalladium(II), palladium(II) acetate/bis (diphenylphosphino) ferrocene and the like. Generally, about 5 to 10 molar percent of palladium is employed. Suitable weak aqueous bases include, but are not limited to, sodium, potassium, lithium, magnesium, cesium, and calcium carbonate and bicarbonate, and the like. For specific and preferred reaction conditions and reagents for some compounds of the present invention, see Examples 1–6 and 10–27 below.

Alternatively, compounds of formula I may be prepared via a Stille coupling, i.e., coupling an aryl chloride, bromide, or triflate to an aryl stannane. For a review of the Stille coupling, see, e.g., *Tetrahedron*, 54:276–285, 1998. Typically, the reaction may be performed by dissolving or suspending an aryl triflate of formula II or III, an aryl stannane of formula II or III, a source of palladium(0), and lithium chloride in a suitable solvent such as 1,4-dioxane. Suitable sources of palladium(0) include those listed above for the Suzuki coupling. Typical reaction temperatures range from ambient to the reflux temperature of the mixture. Preferably, the reaction is performed at the reflux temperature of the mixture. Generally, reaction times range from 1 to about 48 hours but, most typically, the reaction is substantially complete after about 18 hours.

Generally, the aryl stannane is employed in a molar excess relative to the aryl triflate. Such excesses typically range from about 1.01 to about 1.6 equivalents. In addition, about 5 to 10 molar percent of palladium is typically employed. For specific and preferred reaction conditions and reagents for some compounds of the present invention, see Examples 7–9 below.

Since the compounds of this invention are amines, they are basic in nature and accordingly react with any of a number of inorganic and organic acids to form pharmaceutical acid addition salts. Since some of the free amines of the compounds of this invention are typically oils at room temperature, it is preferable to convert the free amines to their pharmaceutical acid addition salts for ease of handling and administration, since the latter are routinely solid at room temperature.

The pharmaceutical acid addition salts of the invention are typically formed by reacting a compound of formula I with an equimolar or excess amount of acid. The reactants are generally combined in a mutual solvent such as diethylether, tetrahydrofuran, methanol, ethanol, isopropanol, ethyl acetate, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like.

The compounds of formula II where A is carbon, D is NH, and E is nitrogen (indazoles) may be prepared from compounds of formula II where A is carbon, D is NH, and E is carbon (indoles) as illustrated in Scheme 2 below where $R^6$ is amino, nitro, chloro, bromo, or hydroxy, and G, J, $R^2$, and $R^3$ are as defined above.

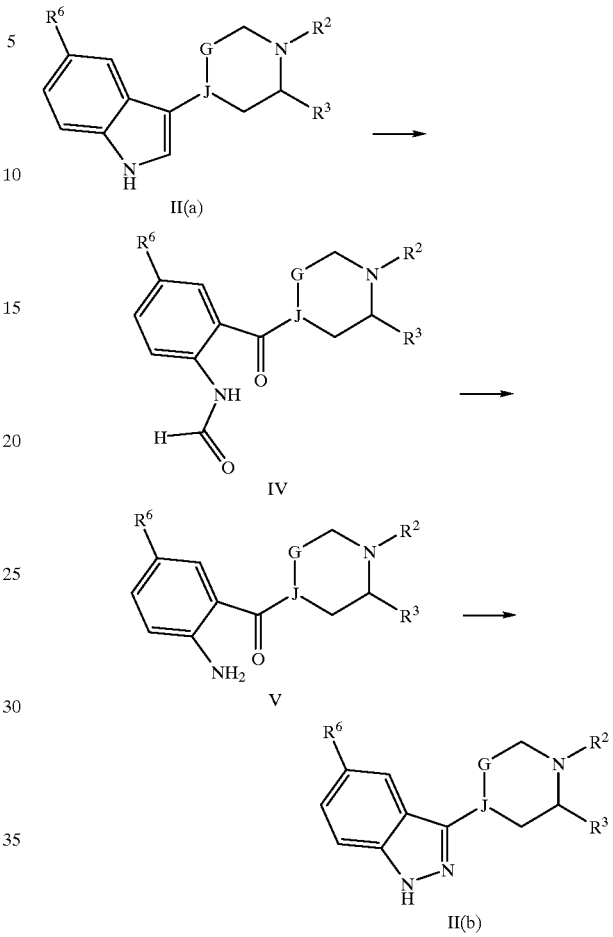

Compounds of formula IV may be prepared by adding a solution of about 2 to 2.5 equivalents of a periodate, typically sodium periodate in water, to a compound of formula II(a) dissolved in a suitable solvent, typically a mixture of methanol and water. Generally, in order to facilitate dissolution in this methanol/water solvent system and to protect the indole NH from oxidation, a salt of a compound of formula II(a) will be employed, e.g., the hydrochloride, or an acid will be added to the reaction mixture to form a salt while reacting, e.g., methanesulfonic acid. The reaction may be performed at temperatures ranging from 0° C. to the reflux temperature of the reaction mixture for from 8 hours to 2 weeks but is usually performed at ambient temperatures. In certain cases, e.g., when $R^6$ is nitro, the deformylation may occur spontaneously during the periodate oxidation step. Thus, the chemistry described in the next paragraph may not be required for all compounds of formula II(a) used in the above reaction.

In cases where a separate step is necessary to remove the formyl group, a compound of formula V may prepared by treating a compound of formula IV with an excess of an appropriate base dissolved in a lower alkanol, typically sodium hydroxide in methanol. This reaction may be performed at temperatures ranging from ambient to the reflux temperature of the mixture for from 1 to 24 hours. Typically, the reaction is performed at about 45° C. for about 2 hours.

The indazoles of formula II(b) may now be prepared by treating a compound of formula V, dissolved in a suitable acidic solvent, with a solution of about 1 equivalent of a nitrite, typically sodium nitrite in water, to create an intermediate diazonium salt. Once the diazonium salt is formed, typically in about 15 minutes to 1 hour, it may be converted to the indazole product by adding this mixture to a large excess of sulfur dioxide, typically as a saturated solution in water. The addition of nitrite may be performed at temperatures ranging from −50° C. to about ambient temperature but is typically performed at about 0° C. The inverse addition of the diazonium salt to the sulfur dioxide solution may also be performed cold as described above but is usually performed at about 3° C. Once the additions are complete, the reaction may be run cold for a short time, e.g., from about 15 minutes to 1 hour, but is then allowed to warm to ambient temperature and stir for an additional 12 to 24 hours.

Compounds of formula II other than indazoles (A is carbon, D is NH, and E is nitrogen) may be prepared by methods known to one of ordinary skill in the art. For example, compounds of formula II where A and E are carbon, D is NH, and $R^2$ is $C_1-C_6$ alkyl may be prepared as taught in U.S. Pat. No. 5,708,008 ('008), the teachings of which are herein incorporated by reference. All other non-indazole compounds of formula II may also be prepared substantially as described for compounds where D is NH and $R^4$ is $C_1-C_6$ alkyl in '008. These syntheses are illustrated below in Scheme 3 where A, D, $R^1$, $R^2_1R^3$ and $R^6$ are as defined above.

Scheme 3

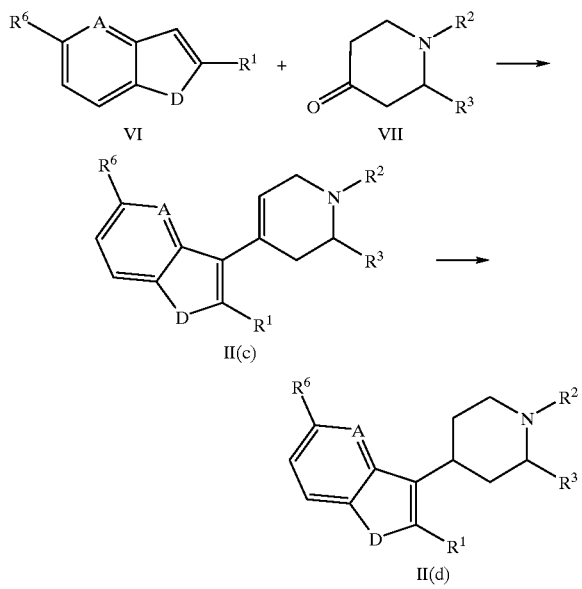

A compound of formula VI may be condense with a compound of formula VII in the presence of a suitable base to give the corresponding compound of formula II (c). For indoles and azaindoles of formula II(c) (D is NH), the reaction may be performed by adding the respective compounds of formula VI and VII to a mixture of an appropriate base (typically sodium or potassium hydroxide) in a lower alkanol, typically methanol or ethanol. About 1 to about 5 equivalents of a compound of formula VII, relative to the compound of formula VI are generally employed. A range of about 1.3 to 2.3 equivalents is preferred. The reaction is typically performed for about 0.25 to 24 hours.

For benzofuran or benzothiophene compounds of formula II(c) (D is oxygen or sulfur) the reaction may be performed by first reacting a benzofuran or benzothiophene of formula VI where $R^6$ is amino or preferably nitro with bromine in acetic acid. The reaction is typically performed at about 50° C. for about 4 hours. After the bromination is substantially complete, the volatiles are then removed under reduced pressure and the residue is subjected to an extractive work-up under basic conditions. The resulting 3-bromobenzothiophene or 3-bromobenzofuran in diethyl ether is then treated with an alkyl lithium, typically n-butyl lithium, in the same solvent, at −78° C. to affect a metal-halogen exchange. After stirring at this temperature for about 1 hour, the reaction mixture is treated with an equivalent of an appropriate compound of formula VII. Once the addition of the compound of formula VII is complete, the reaction mixture is stirred at −78° C. for an additional 3 to 5 hours. It is critical, when $R^1$ is hydrogen, to maintain the reaction mixture at this temperature to avoid equilibration of the anion to the 2-position of the benzofuran or benzothiophene ring. The reaction mixture is then allowed to warm to −20° C. over about 50 minutes. An excess of an appropriate base, preferably sodium or potassium hydroxide, in a lower alkanol, typically methanol or ethanol is then added and the reaction refluxed for 0.25 to 24 hours to provide a benzofuran or benzothiophene compound of formula II(c) where $R^6$ is amino or nitro.

If desired, compounds of formula II(c) may be hydrogenated over a precious metal catalyst to give the corresponding compounds of formula II(d). When $R^6$ is bromo, a catalyst such as sulfided platinum on carbon, platinum oxide, or a mixed catalyst system of sulfided platinum on carbon with platinum oxide may be used to prevent hydrogenolysis of that bromo substituent during the reduction. The hydrogenation solvent may consist of a lower alkanol, such as methanol or ethanol, tetrahydrofuran, or a mixed solvent system of tetrahydrofuran and ethyl acetate. The hydrogenation may be performed at an initial hydrogen pressure of 20 p.s.i. to 80 p.s.i., preferably from 50 p.s.i. to 60 p.s.i., at 0° C. to 60° C., preferably at ambient temperature to 40° C., for 1 hour to 3 days. Additional charges of hydrogen may be required to drive the reaction to completion depending on the specific substrate.

When the hydrogenation is performed with a compound of formula II(c) where $R^6$ is amino or nitro, more vigorous hydrogenation conditions may be used without disrupting the rest of the molecule. For example, a catalyst such as platinum or palladium on carbon may be utilized without substantially effecting deleterious side reactions. Thus, when it is required to employ an intermediate where $R^6$ is amino or nitro, i.e., for the benzofurans and benzothiophenes, such a procedure may be advantageous and preferred.

In general, when $R^6$ is nitro, that nitro group may be reduced to an amine at any convenient point in the syntheses outlined in Schemes 2 and 3 by well known methodology. See, e.g., Larock, "Comprehensive Organic Transformations", pgs. 412–415, VCH Publishers, New York, N.Y., 1989. Additionally, when $R^6$ is nitro in compounds of formula II(c), that nitro group and the double bond may be hydrogenated simultaneously if desired to give a compound of formula II(d) where $R^6$ is amino by many of the methods described by Larock for the nitro group alone. Furthermore, methods for selective reduction of a double bond in the presence of a nitro group are known in the art and one example of that transformation may be found in Preparation 18 below.

When $R^6$ is amino, that amino group may be converted to bromo via the Sandmeyer reaction at any convenient point in the syntheses outlined in Schemes 2 and 3 by procedures taught by M. P. Doyle in *J. Org. Chem.*, 42:2426, 1977. If needed, it is preferred to perform the Sandmeyer reaction after the conversion of a compound of formula II(c) to a compound of formula II(d).

When $R^6$ is hydroxy, that free hydroxy group may have a trifluoromethanesulfonyl group ($SO_2CF_3$) installed by standard procedures known in the art at any convenient point in the syntheses outlined in Schemes 2 and 3. For example, a compound of formula II(c) where $R^6$ is hydroxy may be reacted with trifluoromethanesulfonyl chloride or trifluoromethanesulfonic anhydride in the presence of an appropriate base to give a compound of formula II(c) where $R^6$ is $OSO_2CF_3$. See Preparation 17 below for a detailed description of such a conversion.

When $R^6$ is bromo or chloro, that bromo or chloro group may be converted to a boronic acid ($B(OH)_2$) at any convenient point in the syntheses outlined in Schemes 2 and 3. For example, this conversion may be performed by executing a metal-halogen exchange as described above on a compound of formula II(b) followed by the addition of a source of borate, e.g., triisopropyl borate. See Preparation 3 below for a detailed description of such a conversion.

Furthermore, when $R^6$ is bromo or chloro, that bromo or chloro group may be converted to a stannane via well known procedures at any convenient point in the syntheses outlined in Schemes 2 and 3. For example, this conversion may be performed by reacting a chloro or bromo compound of formula II(d) with a compound of the formula $Sn_2(C_1-C_4$ alkyl$)_6$ in a suitable solvent such as 1,4-dioxane to form a compound of formula II(d) where $R^6$ is $Sn(C_1-C_4$ alkyl$)_3$. Usually, hexamethylditin or hexabutylditin is employed. See Example 7 below for a detailed description of a similar conversion.

Compounds of formula II(a), II(b), II(c), and II(d) where $R^6$ is chloro, bromo, $Sn(C_1-C_4$ alkyl$)_3$, $B(OH)_2$, or $OSO_2CF_3$ prepared as described above may be utilized as in Scheme 1.

The compounds of formula VI where A is carbon and D is NH (indoles), may be prepared by methods well known to one of ordinary skill in the art, such as that generally described in U.S. Pat. No. 4,443,451, the teachings of which are hereby incorporated by reference. While these indoles are generally commercially available, their preparations are also described in Robinson, *The Fischer Indole Synthesis*, Wiley, New York, 1983; Hamel, et al., *Journal of Organic Chemistry*, 59:6372, 1994; and Russell, et al., *Organic Preparations and Procedures International*, 17:391, 1985.

The compounds of formula VI where A is nitrogen, D is NH, $R^1$ is hydrogen, and $R^6$ is hydroxy, may be prepared by methods disclosed in Preparations 4–8 and 11 below. Once prepared, the resulting compound of formula VI (5-hydroxy-4-aza-1H-indole) may be condensed with a compound of formula VII by the procedure described above in Scheme 3. Once condensed, a 5-hydroxy-4-aza-1H-indole compound of formula II(c) or II(d) may have its 5-hydroxy group displaced (after the hydroxy group has been activated for displacement, see Preparation 12) by a suitable source of bromide ion such as phosphorous tribromide. Once prepared, the 5-bromo-4-azaindoles may have a $C_1-C_6$ alkyl group installed at $R^1$ via standard alkylating procedures provided that the indole NH is protected as described above in Greene. For example, 5-bromo-4-aza-1-triisopropylsilylindole may be treated with a base such as a sodium, lithium, or potassium hydride to generate an anion at the 2-position of the 4-azaindole ring system. The addition of a $C_1-C_6$ alkyl chloride, bromide, or iodide to this anionic mixture, followed by removal of the protecting group, affords a compound of formula II(c) II(d) where $R^1$ is $C_1-C_6$ alkyl.

Compounds of formula VI where D is oxygen (benzofurans) or sulfur (benzothiophenes) may be prepared by known procedures such as that described in Scheme 4 below where L is oxygen or sulfur and $R^1$ and $R^6$ are as defined above.

Scheme 4

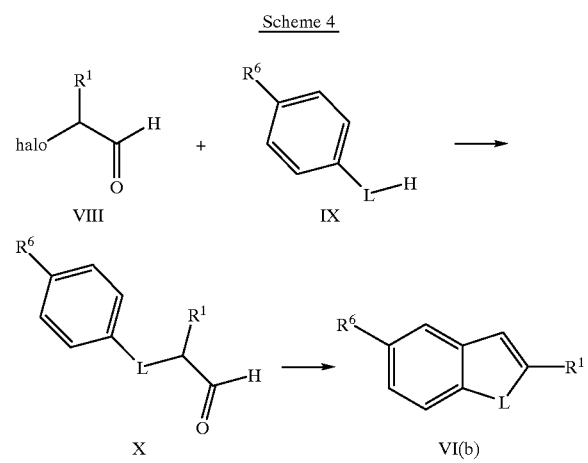

An α-halo-acetaldehyde of formula VIII, optionally protected as the corresponding acetal, may be reacted with an appropriately substituted, commercially available, phenol or thiophenol of formula IX under standard alkylating conditions to provide the corresponding ether or thioether of formula X. This ether or thioether may be converted to a benzofuran or benzothiophene of formula VI(b) by heating a compound of formula X in the presence of an acid, typically polyphosphoric acid or sulfuric acid. When $R^6$ is amino in compounds of formula IX or X, that amino group should be protected with an appropriate amino protecting group as described in Greene. The protecting group may be chosen such that it is hydrolyzed during the cyclization step or, if desired, the unprotected compounds of formula VI(b) where $R^6$ is amino may be prepared in a separate deprotection step if necessary. Furthermore, these amino compounds of formula VI(b) may be converted to the corresponding halo compounds via the Sandmeyer reaction described above.

Compounds of formula VII where $R^2$ and $R^3$ combine, together with the 6 membered ring to which they are attached, to form a 6:5, 6:6, or 6:7 fused bicyclic ring may be prepared from methylvinyl ketone and an appropriate amino-dialkylacetal or -cyclic acetal according to the procedures found in *Tet. Let.*, 24:3281, 1983, and *J.C.S. Perk. I*, 447, 1986. These acetals are generally commercially available or can be synthesized by well known methods in the art from their corresponding commercially available 4-substituted butanals or 5-substituted pentanals. This chemistry is illustrated in Scheme 5, where m is 3,4, or 5 and $R^7$ and $R^8$ are $C_1-C_4$ alkyl or $R^7$ and $R^8$ taken together with the oxygen atoms, to which they are attached, form a 5 or 6 membered cyclic acetal, and n is 0, 1, or 2.

Scheme 5

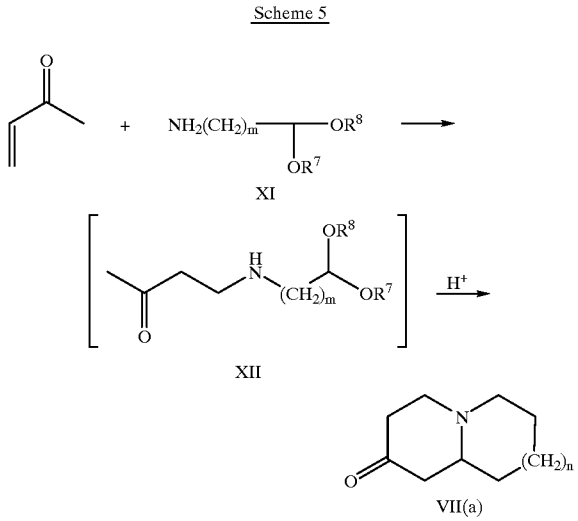

Compounds of formula VII(a) may be prepared by acid treatment of the addition product of methyl vinyl ketone and a compound of formula XI. A diethylacetal of formula XI is a preferred starting material for this reaction ($R^7$ and $R^8$ are ethyl). The reaction may be performed by first dissolving an appropriate aminoacetal of formula XIII in an suitable solvent, typically diethyl ether at 0° C., and then adding approximately 1.7 equivalents of methyl vinyl ketone. Typically the reaction is allowed to stir at 0° C. for approximately 2 hours before acidification by addition of, or extraction with, aqueous hydrochloric acid. Usually, the organic layer is removed before heating the aqueous layer to approximately 100° C. for 1 hour. The resulting 7-octahydroindolizinone, 2-octahydro-2H-quinolizinone, or 4-(1-azabicyclo[5.4.0]undecan)ones of formula VII(a) may be isolated from the reaction mixture by adjusting the pH of the solution to alkaline and extracting with a water immiscible solvent such as ethyl acetate or dichloromethane.

Compounds of formula VII(a) prepared as described in Scheme 5 are racemic and, if used as described in Schemes 1–4 will produce racemic compounds of the invention. Compounds of the invention that are optically enhanced in one enantiomer may be obtained by resolving the compounds of formula VII(a) before use of these compounds as described in Schemes 3. Methods of resolving enantiomeric compounds of this type are well known in the art. For example, resolution can be achieved by use of chiral chromatography. Furthermore, racemic compounds of formula VII(a) may be converted to their corresponding diastereomeric mixture of salts by reaction with a chiral acid such as (+) or (−) tartaric acid. The diastereomers may then be separated and purified by recrystallization. Once separated, the salts may each be converted back to the chiral free base compounds of formula VII(a) by reacting the salts with an aqueous base, such as sodium hydroxide, then extracting the mixture with a common organic solvent. The optical purity in resolved compounds of formula VII(a) is maintained while undergoing the chemistry described in this application to afford optically pure compounds of the invention. As an alternative, when advantageous, the resolution techniques just discussed may be performed at any convenient point in the syntheses described in Schemes 1–3.

The α-halo aldehydes, or corresponding acetals of formula VIII are either commercially available or may be prepared from the corresponding acids or acid halides by methods well known to one of ordinary skill in the art. This chemistry is reviewed by Larock, "Comprehensive Organic Transformations," pages 378–379, VCH Publishers, New York, 1989. Compounds of formula III, VI, VII, VIII, IX, and XI are known in the art and, to the extent not commercially available, are readily synthesized by standard procedures commonly employed in the art such as those described herein.

The optimal time for performing the reactions of Schemes 1–5 may be determined by monitoring the progress of the reaction via conventional chromatographic techniques, e.g., thin layer chromatography and high performance liquid chromatography. Furthermore, it is usually preferred to conduct the reactions of Scheme 1–5 under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The intermediate compounds of this invention are preferably purified before their use in subsequent reactions. The intermediates and final products may be purified when, if in the course of their formation, they crystallize out of the reaction solution. In such a situation, the precipitate may be collected by filtration and washed with an appropriate solvent. Certain impurities may be removed from the organic reaction mixture by aqueous acidic or basic extraction followed by removal of the solvent by extraction, evaporation, or decantation. The intermediates and final products of formula I may be further purified, if desired by common techniques such as recrystallization or chromatography over solid supports such as silica gel or alumina.

The following Preparations and Examples are provided to better elucidate the practice of the present invention and should not be interpreted in any way as to limit the scope of same. Those skilled in the art will recognize that various modifications may be made while not departing from the spirit and scope of the invention. The terms and abbreviations used in the instant Preparations and Examples have their normal meanings unless otherwise designated. For example "° C.", "N", "mmol", "g", "mg", "mL", "M", and MS (FD) refer to degrees Celsius, normal or normality, millimole or millimoles, gram or grams, milligram or milligrams, milliliter or milliliters, molar or molarity, high performance liquid chromatography, and field desorption mass spectrometry respectively.

PREPARATIONS

Preparation 1

5-Bromo-3-(1-Methylpiperidin-4-yl)-1-Triisopropylsilylindole

To a 10° C. slurry of potassium hydride (1.6 g, 14.3 mmol, 35% in mineral oil) in tetrahydrofuran (40 mL) was added neat 5-bromo-3-(1-methyl-4-piperidinyl)indole (2.8 g, 9.5 mmol) portionwise over 30 minutes. The resulting reaction mixture was stirred at 0° C. for 1 hour. Triisopropylsilyl trifluoromethanesulfonate (3.1 mL, 11.4 mmol) was added dropwise over 20 minutes and a slight exotherm was observed. After stirring 2 hours at 0° C., the reaction was quenched with ice chips then diluted with water and methylene chloride. The layers were separated and the aqueous layer was extracted with methylene chloride. The organic extracts were combined, washed with brine, dried over sodium sulfate, and concentrated in vacuo to give 7.4 g of a clear colorless oil. Purification by chromatography (florisil, 50:50 methylene chloride:hexanes, then 100% methylene chloride, then 95:5 methylene chloride:methanol) provided 3.6 g (84.1%) of the title compound. MS(FD) 448, 450 (M+).

Preparation 2

5-Formyl-3-(1-Methylpiperidin-4-yl)-1H-Indole

To a slurry of potassium hydride (20% suspension in mineral oil, 4.30 g, 21.50 mmol) in 80 mL of anhydrous tetrahydrofuran at 0° C. was slowly added dropwise 5-bromo-3-(1-methylpiperidin-4-yl)-1H-indole (6.0 g, 20.5 mmol) in 80 mL of anhydrous tetrahydrofuran. After stirring at 0° C. for 30 minutes, the mixture was cooled to −78° C., and tert-butyl lithium (1.7 M solution in pentane, 45.0 mmol, 26.5 mL) was added dropwise. After 15 minutes, a solution of anhydrous N,N-dimethylformamide (30.7 mmol, 2.4 mL) in 10 mL of anhydrous tetrahydrofuran was added dropwise. The stirred mixture was allowed to warm to room temperature, and was quenched with a 5N aqueous sodium hydroxide solution. The aqueous phase was extracted with diethyl ether, and the ether extracts were separated, washed with brine, dried over sodium sulfate, filtered, concentrated in vacuo and purified by silica gel (flash) chromatography (dichloromethane:methanol 9.5:0.5) to give 2.26 g (45%) of the title product as an oily solid. MS(FD) m/e=242 (M+). EA calculated for $C_{15}SH_{18}N_2O$. ½ $H_2O$: C, 71.69; H, 7.21; N, 11.14. Found: C, 71.38; H, 6.87; N, 11.06.

Preparation 3

3-(1-Methylpiperidin-4-yl)-1H-Indole-5-Boronic Acid

To a slurry of potassium hydride (20% suspension in mineral oil, 0.72 g, 3.58 mmol) in 7 mL of anhydrous tetrahydrofuran at 0° C. was slowly added dropwise 5-bromo-3-(1-methylpiperidin-4-yl)-1H-indole (1.0 g, 3.41 mmol) in 7 mL of anhydrous tetrahydrofuran. After stirring at 0° C. for 30 minutes, the mixture was cooled to −78° C., and tert-butyl lithium (1.7M in pentane, 7.51 mmol, 4.42 mL) was added dropwise. After 15 minutes, a solution of triisopropyl borate (6.82 mmol, 2.0 eq, 1.57 mL) in 2 mL of anhydrous tetrahydrofuran was added dropwise. The stirred mixture was allowed to warm to room temperature, and was quenched with 5N aqueous hydrochloric acid. The aqueous phase was extracted with diethyl ether, and the ether extracts were separated, washed with brine, dried over sodium sulfate, filtered and concentrated in vacuo to give a crude white solid which was treated with hexanes, sonicated for 30 minutes, filtered and dried to give 0.252 g (29%) of the title compound as an amorphous white material which was used without further purification.

Preparation 4

2-Oxo-5-Nitro-6-Methyl-1,2-Dihydropyridine

To a suspension of 2-amino-5-nitro-6-methylpyridine (40.24 g, 260 mmol) was added concentrated sulfuric acid (48 mL). The homogeneous solution was cooled to 0° C., and sodium nitrate (26.97 g, 390 mmol) dissolved in 120 mL of water was added. The reaction mixture was warmed to room temperature over 4 hours, then cooled to 0° C. The resulting ivory precipitate was collected, washed with cold water, and dried at 40° C. in vacuo overnight to provide 39.05 g (97%) of the title compound. EA calculated for $C_6H_6N_2O_3$: C, 46.76; H, 3.92; N, 18.18. Found: C, 46.49; H, 3.94; N, 17.99.

Preparation 5

2-Chloro-5-Nitro-6-Methylpyridine

A mixture of 2-oxo-5-nitro-6-methyl-1,2-dihydropyridine (38.95 g, 253 mmol), phosphorous oxychloride (12.3 mL, 130 mmol), and phosphorous pentachloride (27.9 g, 134 mmol) was heated at 110° C. for 2 hours, whereupon the reaction mixture was charged with an additional portion of phosphorous pentachloride and phosphorous oxychloride (9.9 g and 4.8 mL, respectively). The reaction was stirred 1 hour, then poured into ice-water (600 mL). The brown solid was filtered and washed with cold water, to give 40.88 g of the title compound (94%). MS(m/e): 173 (M+).

Preparation 6

2-Methoxy-5-Nitro-6-Methylpyridine

Sodium metal (8.68 g, 378 mmol) was added to methanol (350 mL) pre-cooled to 0° C. After the sodium completely dissolved, 2-chloro-5-nitro-6-methylpyridine (40.78 g, 236 mmol) was slowly added as a solid. The reaction mixture was heated at reflux temperature overnight, then poured into ice-water. The product was filtered and dried in vacuo overnight to give 29.39 grams of the title compound. (73%).

Preparation 7

2-Methoxy-5-Nitro-6-(2-Dimethylaminoethen-1-yl) pyridine

To 2-methoxy-5-nitro-6-methylpyridine (29.39 g, 175 mmol) dissolved in 300 mL of N,N-dimethylformamide was added dimethylformamide dimethylacetal (120 mL, 896 mmol) and triethylamine (1 mL). The bright red reaction mixture was heated at 120° C. for 2 hours, then concentrated in vacuo to provide 38.90 g of the title compound as a red solid, which was used in Preparation 13 without further purification.

Preparation 8

5-Methoxy-4-Aza-1H-Indole

2-Methoxy-5-Nitro-6-(2-Dimethylaminoethen-1-yl) pyridine (38.78 g, 174 mmol) was dissolved in 1.2 L of ethanol, and charged with 10% palladium on carbon (5.0 g). The mixture was hydrogenated at room temperature under 40 p.s.i. of hydrogen pressure for 4 hours. After filtration through celite followed by chromatography on silica gel (50% ethyl acetate/hexane), the material was recrystallized from ethyl acetate/hexane to provide 19.62 g of the title compound. (76%). MS(m/e): 149 (M+). EA calculated for $C_8H_8N_2O$: C, 64.85; H, 5.44; N, 18.91. Found: C, 64.72; H, 5.33; N, 18.76.

Preparation 9

5-Methoxy-3-(1-Methyl-1,2,3,6-Tetrahydropyridin-4-yl)indole

To a mixture of 5-methoxy-4-aza-1H-indole(7.0 g, 47 mmol) and potassium hydroxide (9.2 g, 165 mmol) in 350 mL of methanol was added 1-methyl-4-piperidone (9.86 mL, 80 mmol) in one portion. The reaction was heated at reflux temperature overnight, and cooled to room temperature. The resulting precipitate was collected, and the filtrate was concentrated to a minimal volume. A second crop of crystals was collected, washed with cold methanol, and combined with the previous crop to afford 9.0 g (79%) of the title compound. MS(m/e): 243 (M+). EA calculated for $C_{14}H_{17}N_3O$: C, 69.11; H, 7.04; N, 17.27. Found: C, 69.22; H, 7.13; N, 17.47.

Preparation 10

5-Methoxy-3-(1-Methylpiperidin-4-yl)indole

5-Methoxy-3-(1-methyl-1,2,3,6-tetrahydropyridin-4-yl) indole (9.00 g, 37 mmol) was dissolved in 190 mL of ethanol/tetrahydrofuran/methanol (10:10:1). 10% palladium on carbon (2.2 g) was added, and the reaction mixture was hydrogenated at 40 p.s.i. in a Parr shaker for 96 hours. The mixture was filtered through celite, the catalyst was washed with ethanol, and the filtrate was concentrated in vacuo. The residue was chromatographed on silica gel (5–10% 2M ammonia-methanol/dichloromethane) to provide 8.79 g (97%) of the title compound. MS(m/e): 245 (M+). EA calculated for $C_{14}H_{19}N_3O$: C, 68.54; H, 7.81; N, 17.13. Found: C, 68.40; H, 7.52; N, 16.90.

Preparation 11

5-Hydroxy-3-(1-Methylpiperidin-4-yl)indole

A solution of 5-methoxy-3-(1-methylpiperidin-4-yl) indole (2.30 g, 9.4 mmol) in 30 mL of 30% hydrobromic acid in acetic acid was heated in a sealed tube at 105° C. for 72 hours. The reaction mixture was cooled to room temperature and concentrated in vacuo. The residue was dissolved in water, and the pH was adjusted to about 13 with 5N aqueous sodium hydroxide. The mixture was concentrated in vacuo, and the residue was chromatographed on a silica gel column, eluting with 20% 2M ammonia in methanol/dichloromethane. After concentrating in vacuo, the residue was dissolved in methanol, charged with Dowex® 50X8-200 ion-exchange resin (25 g) and stirred overnight at room temperature. The mixture was filtered, and the resin was washed with water and methanol. The Dowex® resin was stirred overnight in 100 mL of 2M ammonia in methanol and filtered. The filtrate was concentrated in vacuo to provide 1.84 g (85%) of the title compound, which was used without further purification in Preparation 17. EA calculated for $C_{13}H_{17}N_3O$: C, 67.53; H, 7.36; N, 18.18. Found: C, 67.24; H, 7.37; N, 18.38.

Preparation 12

5-Triflate-3-(1-Methylpiperidin-4-yl)indole

To a solution of 5-hydroxy-3-(1-methylpiperidin-4-yl) indole (900 mg, 3.89 mmol) cooled to 0° C. in pyridine (80 mL) was added trifluoromethanesulfonic anhydride (1.71 mL, 10.13 mmol). The reaction was allowed to warm to room temperature, and after 4 hours was concentrated in vacuo. The residue was partitioned between 3:1 chloroform/isopropyl alcohol and saturated aqueous sodium bicarbonate, extracted with 3:1 chloroform/isopropyl alcohol, washed with brine, dried with sodium sulfate, filtered and concentrated in vacuo. Silica gel chromatography, eluting with 20% 2M ammonia in methanol/dichloromethane, provided 1.12 g (79%) of the title compound. mp=171–174° C. MS(m/e): 363 (M+). EA calculated for $Cl_4H_{16}F_3N_3O_3S \cdot 0.25 H_2O$: C, 45.71; H, 4.52; N, 11.42. Found: C, 45.63; H, 4.45; N, 11.20.

Preparation 13

5-Nitro-3-(1-Methylpiperidin-4-yl)-1H-Indole

Triethylsilane (4.7 ml, 29.5 mmol) was added dropwise to a 0° C. solution of 5-nitro-3-(1-methyl-4-tetrahydropyridinly)indole (7.6 g, 29.5 mmol) in trifluoroacetic acid (50 ml). This resulting solution was stirred 2.5 hours at 0° C. then warmed to room temperature. The reaction mixture was concentrated in vacuo. The residue was dissolved in methylene chloride, cooled on an ice bath and 5N aqueous sodium hydroxide (110 ml) was added. The heterogeneous mixture was stirred 1 hour and the resulting precipitate was filtered and washed with water. Drying under vacuum yielded 5.0 g (65.3%) of the title compound. mp 200° C.–202° C. EA calculated for $C_{14}H_{17}N_3O_2$: C, 64.85; H, 6.61; N, 16.20. Found: C, 64.72; H, 6.48; N, 16.11.

Preparation 14

4-(2-Amino-5-Nitrobenzoyl)-1-Methylpiperidine

A solution of sodium metaperiodate (1.8 g, 8.5 mmol) in water (100 mL) was added dropwise to a solution of 5-nitro-3-(1-methyl-4-piperidinyl)indole (1.0 g, 3.9 mmol) and methanesulfonic acid (260 μL, 4.0 mmol) in methanol (50 mL). The solution was stirred for 2 hours at room temperature then additional sodium metaperiodate (830 mg, 3.9 mmol) was added. The resulting solution was stirred for 13 days at room temperature. The reaction mixture was poured onto 10% aqueous sodium bicarbonate solution (300 mL) and extracted with ethyl acetate. The ethyl acetate extracts were washed with 10% aqueous sodium bicarbonate solution, water, and brine, and dried over sodium sulfate. The aqueous washes were extracted with methylene chloride and dried over sodium sulfate. The dried organic extracts were filtered, combined, and concentrated in vacuo to give 900 mg of a yellow solid. Purification by flash chromatography (silica gel, methylene chloride then methylene chloride:methanol:ammonium hydroxide, 100:4:0.5) gave 685 mg (67.2%) of the title compound. mp 131° C.–132° C. EA calculated for $C_{13}H_{17}N_3O_3$: C, 59.30; H, 6.51; N, 15.96. Found: C, 59.01; H, 6.47; N, 15.79.

Preparation 15

5-Nitro-3-(1-Methylpiperidin-4-yl)-1H-Indazole

To a −5° C. solution of 4-(2-amino-5-nitrobenzoyl)-1-methylpiperidine (570 mg, 2.2 mmol) in 9.6N aqueous hydrochloric acid (10 mL) was added dropwise a solution of sodium nitrite (164 mg, 2.4 mmol) in water (3 mL). This resulting diazonium salt solution was stirred 10 minutes at −5° C. then added dropwise to a −5° C. solution of stannous chloride dihydrate (1.95 g, 8.6 mmol) in 12N aqueous hydrochloric acid (6 mL). The resulting solution was stirred 2 hours at −3° C., basified with 1N aqueous sodium hydroxide (190 mL) and extracted exhaustively with ethyl acetate and methylene chloride. The combined organic extracts were dried over sodium sulfate, filtered, and concentrated in vacuo to give 420 mg of a brown residue. Purification by radial chromatography (silica gel, 2000 micron rotor, methylene chloride:methanol:ammonium hydroxide, 100:10:1) gave 177 mg (31.4%) of the title compound. The product was crystallized as the hydrochloride salt. EA calculated for $C_{13}H_{17}ClN_4O_2$: C, 52.62; H, 5.77; N, 18.88. Found: C, 52.39; H, 5.96; N, 18.77.

Preparation 16

5-Amino-3-(1-Methylpiperidin-4-yl)-1H-Indazole

A mixture of 5-nitro-3-(1-methylpiperidin-4-yl)-1H-indazole (287 mg, 1.1 mmol), 5N aqueous hydrochloric acid (0.5 mL), water (5ml), and methanol (15 mL) was warmed to give a homogeneous solution. Palladium (86 mg, 5% on carbon) was added to the solution and the resulting mixture was stirred under an atmosphere of hydrogen gas for 24 hours. The palladium catalyst was filtered and the filtrate was concentrated in vacuo. The residue was slurried in methylene chloride and 5N aqueous sodium hydroxide then extracted with chloroform/isopropanol (3:1). The organic extracts were dried over sodium sulfate, filtered, and concentrated in vacuo to give 261 mg of a light brown foam. Purification by radial chromatography (silica gel, 2000 micron rotor, methylene chloride:methanol:ammonium hydroxide, 100:10:1) gave 223 mg (87.8%) of a brown oil. The product was crystallized as the dihydrochloride salt. EA calculated for $C_{13}H_{20}Cl_2N_4$: C, 51.49; H, 6.65; N, 18.48. Found: C, 51.44; H, 6.76; N, 18.47.

Preparation 17

5-Bromo-3-(1-Methyl-1,2,3,6-Tetrahydropyridin-4-yl)-1H-Indole

To a solution of 56.11 gm (306 mmol) potassium hydroxide in 300 mL methanol was added 38 mL (306 mMol) 1-methyl-4-piperidone followed by 30.0 gm (153 mMol) 5-bromo-1H-indole. The reaction mixture was stirred at the reflux temperature of the mixture for 18 hours. The reaction mixture was then cooled to ambient and diluted with 1.5 L water. The resultant white solid was filtered, washed sequentially with water and diethyl ether, and then dried under vacuum to give 44.6 gm of the title compound. (100%).

Preparation 18

5-Bromo-3-(1-Methylpiperidin-4-yl)-1H-Indole

To a solution of 5-bromo-3-(1-methyl-1,2,3,6-tetrahydro-4-pyridinyl)-1H-indole (44.6 g, 153 mmol) in 1.95 L tetrahydrofuran was added 9.0 gm platinum oxide. The reaction mixture was hydrogenated with an initial hydrogen pressure of 60 p.s.i. at ambient temperature for 24 hours. The reaction mixture was filtered and the filtrate concentrated under reduced pressure. The residue was recrystallized from acetonitrile to give 32.6 gm (73.7%) of the title compound as a white solid. MS(m/e): 293($M^+$). EA calculated for $C_{14}H_{17}N_2Br$: C, 57.32; H, 5.96; N, 9.69. Found: C, 57.35; H, 5.84; N, 9.55.

Preparation 19

7-Octahydroindolizinone

Methylvinyl ketone (18.0 g, 256 mmol) was added dropwise to a solution of the 4,4-diethoxybutylamine (24.8 g, 154 mmol) in diethyl ether at 0° C. and stirred for one hour. The reaction was allowed to warm to room temperature and stir for 2 hours. The reaction was poured into 350 ml of 2N hydrochloric acid and the layers were separated. The aqueous layer was heated on a steam bath for 1 hour and then allowed to stir at 40° C. for 18 hours. The reaction was made basic with a sodium hydroxide solution and then extracted with methylene chloride. The extracts were dried over sodium sulfate and concentrated to give 20 g of an orange oil. This oil was distilled in vacuo at 74–84° C./5 mmHg to give 6.68 g of racemic product. (31%). MS(FD)(m/e): 139. $^1$H-NMR.

Preparation 20

Resolution of Racemic 7-Octahydroindolizinone
Step 1: Preparation of the (+)-Ditoluoyl Tartaric Acid Salts of 7-Octahydroindolizinone The (+)-ditoluoyl tartaric acid monohydrate (19.7 g, 49 mmol) was dissolved in 100 ml of warm methanol and the racemic 7-octahydroindolizinone (6.86 g, 49 mmol) in 25 ml of methanol was added. The reaction was thoroughly mixed and allowed to stand at room temperature for about 18 hours. No precipitate had formed so the material was concentrated by boiling and ethyl acetate was added. At the point where solid began to form, the reaction was cooled to room temperature and a precipitate formed. This material was collected by filtration. The filter cake was recrystallized twice from methanol/acetonitrile to give 7.87 g a product which was approximately a 2:1 mixture of diastereomers. (31%). EA calculated for $C_8H_{13}NO.C_{20}H_{18}O_8$: Theory: C, 63.99; H, 5.95; N, 2.67. Found: C, 63.92; H, 5.98; N, 2.55. OR(DMSO, C=1.0) (α): 589 nm 72.60; 365 nm 393.4°.
Step 2: Preparation of the Chiral 7-Octahydroindolizinone Free Amine The (+)-ditoluoyl tartaric acid salt of 7-octahydroindolizinone (7.42 g, 14 mmol) from Step 1 was suspended in methylene chloride/0.5 M sodium hydroxide solution and stirred until no solid was visible. The layers were separated and the aqueous layer extracted with methylene chloride. The combined organic extracts were dried over sodium sulfate and concentrated to give 2.00 g of a light yellow oil. (100%). MS(FD)(m/e): 139.

Preparation 21

2-Octahydro-2H-Quinolizinone
Step 1: Preparation of 2-(3-Cyanopropyl)-1,3-Dioxolane In a flame dried flask fitted with a nitrogen inlet, magnetic stirrer, and oil bath was dissolved the 2-(3-chloropropyl)-1,3-dioxolane (25.4 g, 169 mmol) in 70 ml of dimethylsulfoxide. Sodium cyanide (9.1 g, 186 mmol) in 100 ml of dimethylsulfoxide was added and the mixture was heated to 80° C. for 18 hours. The reaction was cooled to room temperature then poured onto ice water and stirred for 1 hour. The mixture was extracted thoroughly with diethyl ether, testing the aqueous after each extraction by TLC for the presence of product. The ether was washed with brine, dried over sodium sulfate, and concentrated in vacuo to give a colorless oil. The oil was purified by silica gel chromatography (50/50 ethyl acetate/hexane) to give 19.2 g of product. (80.7%). EA calculated for $C_7H_{11}NO_2$: Theory: C, 59.33; H, 7.63; N, 9.87. Found: C, 59.56; H, 7.85; N, 9.92. MS(FD+) (m/e): 142.
Step 2: Preparation of 2-(4-Aminobutyl)-1,3-Dioxolane To a solution of 14.5 gm (10.3 mmol) 2-(3-Cyanopropyl)-1,3-dioxolane in anhydrous ammonia and ethanol was added 5% ruthenium on aluminum oxide. The reaction mixture was hydrogenated with an initial hydrogen pressure of 100 p.s.i. at ambient temperature for 32 hours. The reaction mixture was filtered and the filtrate concentrated under reduced pressure. The residue was purified by silica gel chromatography to give 12.0 gm (80.5%) of the product. MS (FD+) (m/e): 146.
Step 3: Preparation of 2-Octahydro-2H-Quinolizinone The 2-(4-aminobutyl)-1,3-dioxolane (2.45 g, 16.9 mmol) and methylvinyl ketone (2.4 ml, 28.7 mmol) were converted to product by the procedure of Preparation I to yield 100 mg. (3.85%). MS(FD+) (m/e): 153.

Preparation 22

3-(1,2,3,4,5,8-Hexahydroindolizin-7-yl)-5-Nitro-1H-Indole

A mixture of 5-nitro-1H-indole (4.48 g, 27.6 mmol) and and 7-octahydroindolizinone (5.0 g, 35.9 mmol) in methanolic potassium hydroxide (10% potassium hydroxide in 50 mL of methanol) was heated to reflux for 3.5 hours. The reaction was diluted with water and the precipitate was collected by filtration. The filter cake was triturated with hot diethyl ether and filtered. The filter cake was recrystallized from methanol and dried to give 2.99 g of the title compound. (38.5%). Calculated for $C_{16}H_{17}N_3O_2$: Theory: C, 67.83; H, 6.05; N, 14.83. Found: C, 68.07; H, 6.27; N, 14.82. MS(FD) (m/e): 283.

Preparation 23

3-(Octahydroindolizin-7-yl)-5-Amino-1H-Indole

The 3-(1,2,3,4,5,8-hexahydroindolizin-7-yl)-5-nitro-1H-indole (2.21 g, 6.90 mmol) was dissolved in 95 ml of ethanol and 50 ml of tetrahydrofuran. 5% palladium over carbon was added (550 mg) and the mixture was placed under an atmosphere of hydrogen, at an initial pressure of 60 psi, at room temperature, for 24 hours. The reaction mixture was filtered and the filtrate concentrated under reduced pressure to give 1.51 g of a purple foam. (85%).

Preparation 24

3-(1,2,3,4,5,8-Hexahydroindolizin-7-yl)-5-Chloro-1H-Indole

5-Chloro-1H-indole (1.00 g, 6.63 mmol) and 7-octahydroindolizinone (1.39 g, 9.95 mmol) were converted to product by the procedure of Preparation 17 to give 595 mg. (33.1%). EA calculated for $C_{16}H_{17}N_2Cl$: C, 70.45; H, 6.28; N, 10.27. Found: C, 70.60; H, 6.46; N, 10.28. MS(FD) (m/e): 272.

Preparation 25

3-Bromo-5-Chlorobenzothiophene

To a solution of 0.30 gm (1.77 mMol) 5-chlorobenzothiophene 1.0 mL acetic acid was added a solution of 0.31 gm (1.95 mMol) bromine in 1.0 mL acetic acid under a nitrogen atmosphere. The reaction was heated to 50° C. for 4 hours at which time the volatiles were removed under reduced pressure. The residue was partitioned between dichloromethane and aqueous sodium bicarbonate. The phases were separated and the organics were washed with saturated aqueous sodium chloride, dried over sodium sulfate and concentrated under reduced pressure to give 0.335 gm (76%) of the title compound as a tan solid. m.p.=85–86° C. MS(FD): m/e=249 (M+2).

EXAMPLE

Example 1

5-(4-Fluorophenyl)-3-(1-Methylpiperidin-4-yl)-4-Aza-1H-Indole

O-Trifluoromethanesulfonyl-3-(1-methylpiperidin-4-yl)-5-hydroxy-4-aza-1H-indole (150 mg, 0.412 mmol), 4-fluorophenylboronic acid (87 mg, 0.619 mmol), tetrakis (triphenylphosphine)palladium(0) (48 mg, 0.041 mmol), 4 mL of 2M aqueous sodium bicarbonate, and 30 mL of tetrahydrofuran were placed in a round bottom flask. The mixture was heated to reflux (about 75° C.) and allowed to stir for about 18 hours. The reaction was poured into 3:1 chloroform:isopropyl alcohol, extracted three times each with 1N aqueous sodium hydroxide and brine, dried over sodium sulfate, filtered, and concentrated in vacuo. The residue was chromatographed (silica gel, 0–10% methanol/dichloromethane) to give 87.9 mg of the title compound. (79%). MS(FD) m/e 309.6 (M+). EA calculated for $C_{19}H_{20}FN_3$: C, 73.79; H, 6.47; N, 13.59. Found: C, 73.69; H, 6.73; N, 13.40.

Example 2

5-(Thien-2-yl)-3-(1-Methylpiperidin-4-yl)-4-Aza-1H-Indole

O-Trifluoromethanesulfonyl-3-(1-methylpiperidin-4-yl)-5-hydroxy-4-aza-1H-indole (158 mg, 0.435 mmol) and 2-thiopheneboronic acid (83 mg, 0.653 mmol) were converted to 86 mg of the title compound by the procedure of Example 1 except that a wash with 3:1 chloroform:isopropanol was performed between the base and brine and the solvent system for chromatography was 0–5% methanol/dichloromethane. (67%). MS(FD) m/e 297.2 (M+). EA calculated for $C_{17}H_{19}SN_3$: C, 68.69; H, 6.40; N, 14.14. Found: C, 69.02; H, 6.49; N, 14.23.

Example 3

5-(Thien-3-yl)-3-(1-Methylpiperidin-4-yl)-4-Aza-1H-Indole

O-Trifluoromethanesulfonyl-3-1-methylpiperidin-4-yl)-5-hydroxy-4-aza-1H-indole (195 mg, 0.536 mmol) and 3-thiopheneboronic acid (103 mg, 0.805 mmol) were converted to 114 mg of the title compound by the procedure of Example 2 except that the solvent system for chromatography was 0–10% methanol/dichloromethane. (71%). MS(FD) m/e 298.0 (M+). EA calculated for $C_{17}H_{19}SN_3$: C, 68.65; H, 6.44; N, 14.13. Found: C, 68.74; H, 6.70; N. 13.98.

Example 4

5-(Naphth-2-yl)-3-(1-Methylpiperidin-4-yl)-4-Aza-1H-Indole

O-Trifluoromethanesulfonyl-3-(1-methylpiperidin-4-yl)-5-hydroxy-4-aza-1H-indole (164 mg, 0.450 mmol) and 2-naphthylboronic acid (124 mg, 0.720 mmol) were converted to 141 mg of the title compound by the procedure of Example 3. (91%). MS(FD) m/e 341.8 (M+). EA calculated for $C_{23}H_{23}N_3$: C, 80.94; H, 6.74; N, 12.32. Found: C, 88.11; H, 6.87; N, 12.27.

Example 5

5-(4-Fluoronaphth-1-yl)-3-(1-Methylpiperidin-4-yl)-4-Aza-1H-Indole

O-Trifluoromethanesulfonyl-3-(1-methylpiperidin-4-yl)-5-hydroxy-4-aza-1H-indole (160 mg, 0.441 mmol) and 4-fluoronaphth-1-ylboronic acid (134 mg, 0.71 mmol) were converted to 134 mg of the title compound by the procedure of Example 3. (85%). MS(FD) m/e 359.8 (M+). EA calculated for $C_{23}H_{22}FN_3$: C, 76.88; H, 6.13; N, 11.70. Found: C, 77.15; H, 6.21; N, 11.62.

Example 6

5-(3,5-Di(trifluoromethyl)phenyl)-3-(1-Methylpiperidin-4-yl)-4-Aza-1H-Indole

O-Trifluoromethanesulfonyl-3-(1-methylpiperidin-4-yl)-5-hydroxy-4-aza-1H-indole (160 mg, 0.441 mmol) and 3,5-di(trifluoromethyl)phenylboronic acid (183 mg, 0.71 mmol) were converted to 171 mg of the title compound by the procedure of Example 3. (91%). MS(FD) m/e 427.6 (M+). EA calculated for $C_{21}H_{19}F_6N_3$: C, 59.02; H, 4.45; N, 9.84. Found: C, 59.31; H, 4.69; N, 9.83.

Example 7

5-(Quinolin-4-yl)-3-(1-Methylpiperidin-4-yl)-4-Aza-1H-Indole

O-Trifluoromethanesulfonyl-3-(1-methylpiperidin-4-yl)-5-hydroxy-4-aza-1H-indole (239 mg, 0.658 mmol), tetrakis (triphenylphosphine)palladium(0) (76 mg, 0.065 mmol), dried lithium chloride (167 mg, 3.95 mmol), 4-chloroquinoline (108 mg, 0.658 mmol), hexamethylditin (215 mg, 0.658 mmol), and 15 mL of 1,4-dioxane were placed in a flask and heated to reflux (about 105° C.). The reaction was stirred for about 18 hours before 50 mL of 8M aqueous potassium fluoride solution was added. The solution was extracted with 3:1 chloroform:isopropanol and brine, dried over sodium sulfate, filtered, and concentrated in vacuo. The residue was purified by silica gel flash chromatography (0–10% methanol:dichloromethane) to give 103 mg of the title compound. (46%). MS(FD) m/e 343.2 (M+H). EA calculated for $C_{22}H_{22}N_4$: C, 77.16; H, 6.48; N, 16.36. Found: C, 76.98; H, 6.55; N, 16.29.

Example 8

5-(Benzimidazol-2-yl)-3-(1-Methylpiperidin-4-yl)-4-Aza-1H-Indole

O-Trifluoromethanesulfonyl-3-(1-methylpiperidin-4-yl)-5-hydroxy-4-aza-1H-indole (150 mg, 0.413 mmol) and 1-t-butyloxycarbonyl-2-chlorobenzimidazole (104 mg, 0.413 mmol) were converted to the title compound by the procedure of Example 7 except that after chromatography there was a mixture of protected and de-protected products. Therefore, 80 mg of the mixture was dissolved in 20 mL of dichloromethane and 1 mL of trifluoroacetic acid was added. The mixture was stirred for 2 hours and then taken up in water. The reaction was partitioned between 3 mL of 1N aqueous sodium hydroxide and 3 mL of 3:1 chloroform:isopropanol to give 51.2 mg. (37%). MS(FD) m/e 331.8 (M+).

Example 9

5-(Pyrid-2-yl)-3-(1-Methylpiperidin-4-yl)-4-Aza-1H-Indole

O-Trifluoromethanesulfonyl-3-(1-methylpiperidin-4-yl)-5-hydroxy-4-aza-1H-indole (150 mg, 0.413 mmol), palladium(II)acetate (9.2 mg, 0.041 mmol), 1,1'-bis(diphenylphosphino)ferrocene (45 mg, 0.083), lithium chloride (105 mg, 2.48 mmol), and 15 mL of 1,4-dioxane were combined and stirred for 5 minutes. 2-Tributylstannylpyridine (197 µL, 0.537 mmol) was added and the mixture was heated to reflux (about 105° C.) and stirred for about 18 hours. 50 mL of 8M aqueous potassium fluoride solution was added and the solution was extracted with 3:1 chloroform:isopropanol and brine and concentrated in vacuo. The residue was purified by silica gel flash chromatography (0–20% methanol:dichloromethane) to give 31.1 mg of the title compound. (26%). MS(FD) m/e 293.1 (M+).

Example 10

5-Phenyl-3-(1-Methylpiperidin-4-yl)-1H-Indole

A mixture of 5-bromo-3-(1-methylpiperidin-4-yl)-1-(triisopropylsilyl)-indole (0.600 g, 1.34 mmol), phenylboronic acid (0.171 g, 1.40 mmol), tetrakis(triphenylphosphine)palladium(0) (0.077 g, 0.067 mmol), and 2M aqueous sodium carbonate solution (2 mL) in toluene (15 mL) was heated at reflux overnight. The solution was allowed to cool to room temperature, diluted with ethyl acetate and brine, the organic phase was separated, dried over sodium sulfate, filtered and concentrated in vacuo. The residue was purified by silica gel (flash) chromatography (dichloromethane:methanol:aqueous ammonium hydroxide 4.5:0.5:0.2) to give 0.128 g of 5-phenyl-3-(1-methylpiperidin-4-yl)-1-(triisopropylsilyl)-indole (22%) as an oil, which was desilylated by dissolving in 1 mL of tetrahydrofuran and treating with tetrabutylammonium fluoride (1M solution in tetrahydrofuran, 4 mL) with stirring at room temperature for 3 hours. The mixture was concentrated in vacuuo, and the resulting oil was purified by silica gel (flash) chromatography (eluting with 500 mL dichloromethane, followed by dichloromethane:methanol:aqueous ammonium hydroxide 4.5:0.5:0.1) to give the title compound (0.045 g) as an amorphous white solid. FDMS m/e=289 (M+). EA calculated for $C_{20}H_{22}N_2$: C, 82.72; H, 7.64; N, 9.65. Found: C, 82.19; H, 7.37; N, 9.75.

Example 11

5-(4-Chlorophenyl)-3-(1-Methylpiperidin-4-yl)-1H-Indole

The title compound was prepared by the procedure of Example 10, beginning with 5-bromo-3-(1-methylpiperidin-4-yl)-1-(triisopropylsilyl)-indole (0.500 g, 1.11 mmol), 4-chlorophenylboronic acid (0.183 g, 1.17 mmol), tetrakis(triphenylphosphine)palladium(0) (0.064 g, 0.056 mmol), and 2M aqueous sodium carbonate solution (2 mL) in toluene (15 mL) to give 0.200 g of 5-(4-chlorophenyl)-3-(1-nethylpiperidin-4-yl)-1-(triisopropylsilyl)-indole (40%) as a white solid, which was desilylated by dissolving in 1 mL of tetrahydrofuran and treating with tetrabutylammonium fluoride (1M in tetrahydrofuran, 4 mL) to give the title compound (0.112 g, 83%) as an amorphous solid. FDMS m/e=325 ($M^+$). EA calculated for $C_{20}H_{21}N_2Cl.½ H_2O$: C, 71.95; H, 6.64; N, 8.39. Found: C, 72.09; H, 6.68; N, 8.48.

Example 12

5-(4-Methoxyphenyl)-3-(1-Methylpiperidin-4-yl)-1H-Indole

The title compound was prepared by the procedure of Example 10, beginning with 5-bromo-3-(1-methylpiperidin-4-yl)-1-(triisopropylsilyl)-indole (0.600 g, 1.34 mmol), 4-methoxyphenylboronic acid (0.213g, 1.40 mmol), tetrakis(triphenylphosphine)palladium(0) (0.077g, 0.067 mmol), and 2M aqueous sodium carbonate solution (2 mL) in toluene (15 mL) to give 0.150 g of 5-(4-methoxyphenyl)-3-(1-methylpiperidin-4-yl)-1-(triisopropylsilyl)-indole (24%) as a solid, which was desilylated by dissolving in 1 mL of tetrahydrofuran and treating with tetrabutylammonium fluoride (1M in tetrahydrofuran, 4 mL) to give the title compound (0.050 g, 45%) as an amorphous solid. FDMS m/e 320 ($M^+$). EA calculated for $C_{21}H_{24}N_2O.⅛ H_2O$: C, 78.17; H, 7.57; N, 8.68. Found: C, 78.13; H, 7.92; H, 8.43.

Example 13

5-(Benzo[b]thien-2-yl)-3-(1-Methylpiperidin-4-yl)-1H-Indole

The title compound was prepared by the procedure of Example 10, beginning with 5-bromo-3-(1-methylpiperidin-4-yl)-1-(triisopropylsilyl)-indole (0.700 g, 1.56 mmol), benzo[b]thiophene-2-boronic acid (0.336 g, 1.87 mmol), tetrakis(triphenylphosphine)palladium(0) (0.090 g, 0.078 mmol), and 2M aqueous sodium carbonate solution (3 mL) in toluene (15 mL) to give 0.160 g of 5-(2-benzo[b]thienyl)-3-(1-methylpiperidin-4-yl)-1-(triisopropylsilyl)-indole (22%) as a solid, which was desilylated by dissolving in 1 mL of tetrahydrofuran and treating with tetrabutylammonium fluoride (1M in tetrahydrofuran, 7 mL) to give the title compound (0.048 g, 43%) as an amorphous solid. FDMS m/e=346 (M$^+$). EA calculated for $C_{22}H_{22}N_2S$.¼ $H_2O$: C, 75.28; H, 6.46; N, 7.98. Found: C, 75.11; H, 6.84; N, 7.91.

Example 14

5-(Pyrid-3-yl)-3-(1-Methylpiperidin-4-yl)-1H-Indole

A mixture of 3-(1-methylpiperidin-4-yl)-1H-indole-5-boronic acid (0.200g, 0.78 mmol), 3-bromopyridine (0.117 g, 0.74 mmol), 1,1'-[bis(diphenylphosphino)ferrocene]-dichloropalladium(II) complex with dichloromethane (Pd(dppf)Cl$_2$.CH$_2$Cl$_2$) (0.03 g, 0.37 mmol), and 2M aqueous sodium carbonate solution (2 mL) in 7 mL of tetrahydrofuran was heated at reflux, with stirring, overnight. The mixture was allowed to cool to room temperature, diluted with ethyl acetate and 2N aqueous sodium hydroxide solution, and the organic phase was separated, washed with brine solution, dried over sodium sulfate, concentrated in vacuo and purified by silica gel (flash) chromatography (solvent gradient: 100% dichloromethane—25:2 dichloromethane: methanol/aqueous ammonium hydroxide) to give 0.114 g (53%) of the title compound as an amorphous pink solid. FDMS m/e=291 (M$^+$). EA calculated for $C_{19}H_{21}N_3$: C, 78.32; H, 7.26; N, 14.42. Found: C, 78.39; H, 7.39; N, 14.36.

Example 15

5-(Thiazol-2-yl)-3-(1-Methylpiperidin-4-yl)-1H-Indole

The title compound was prepared by the procedure of Example 14, beginning with 3-(1-methylpiperidin-4-yl)-1H-indole-5-boronic acid (0.200g, 0.78 mmol), 2-bromothiazole (0.077 g, 0.74mmol), Pd(dppf)Cl$_2$.CH$_2$Cl$_2$ (0.018 g, 0.022 mmol), and 2M aqueous sodium carbonate solution (2 mL) in 6 mL of tetrahydrofuran to give 0.078 g (35%) of the title compound as an amorphous tan solid. FDMS m/e=297 (M$^+$). EA calculated for $C_{17}H_{19}N_3S$.½ $H_2O$ C, 67.63; H, 6.51; N, 13.91. Found: C, 67.91; H, 6.54; N, 13.37.

Example 16

5-(Quinolin-3-yl)-3-(1-Methylpiperidin-4-yl)-1H-Indole

The title compound was prepared by the procedure of Example 14, beginning with 3-(1-methylpiperidin- 4-yl)-1H-indole-5-boronic acid (0.200 g, 0.78 mmol), 3-bromoquinoline (0.154 g, 0.74 mmol), Pd(dppf)Cl$_2$.CH$_2$Cl$_2$ (0.03 g, 0.037 mmol), and 2M aqueous sodium carbonate solution (2 mL) in 7 mL of tetrahydrofuran to give 0.194 g (77%) of the title compound as an amorphous pink solid. FDMS m/e=341 (M$^+$). EA calculated for $C_{23}H_{23}N_3$: C, 80.90; H, 6.79; N, 12.31.

Found: C, 80.69; H, 6.65; N, 12.07.

Example 17

5-(Benzothiazol-2-yl)-3-(1-methylpiperidin-4-yl)-1H-Indole

The title compound was prepared by the procedure of Example 14, beginning with 3-(1-methylpiperidin-4-yl)-1H-indole-5-boronic acid (0.200 g, 0.78 mmol), 2-chlorobenzothiazole (0.126 g, 0.74 mmol), Pd(dppf)Cl$_2$.CH$_2$Cl$_2$ (0.018 g, 0.022 mmol), and 2M aqueous sodium carbonate solution (2 mL) in 6 mL of tetrahydrofuran to give 0.150 g (59%) of the title compound as an amorphous tan solid. FDMS m/e=347 (M$^+$). EA calculated for $C_{21}H_{21}N_3S$.½ $H_2O$: C, 70.75; H, 6.22; N, 11.79. Found: C, 71.03; H, 6.39; N, 11.60.

Example 18

5-(Benzimidazol-2-yl)-3-(1-Methylpiperidin-4-yl)-1H-Indole

The title compound was prepared by the procedure of Example 14, beginning with 3-(1-methylpiperidin-4-yl)-1H-indole-5-boronic acid (0.250 g, 0.97 mmol), 2-chlorobenzimidazole (0.140 g, 0.92 mmol), Pd(dppf)Cl$_2$ CH$_2$Cl$_2$ (0.023 g, 0.028 mmol), and 2M aqueous sodium carbonate solution (2 mL) in 6 mL of tetrahydrofuran to give 0.130 g (43%) of the title compound as an amorphous tan solid. FDMS m/e=330 (M$^+$). EA calculated for $C_{21}H_{22}N_4$.¾ $H_2O$ C, 73.33; H, 6.89; N, 16.29. Found: C, 73.79; H, 6.66; N, 16.08.

Example 19

5-(Indol-2-yl)-3-(1-Methylpiperidin-4-yl)-1H-Indole Oxalate

The title compound was prepared by the procedure of Example 14, beginning with 3-(1-methylpiperidin-4-yl)-1H-indole-5-boronic acid (0.600 g, 2.30 mmol), 2-iodo-1-(phenylsulfonyl)indole (0.850 g, 2.20 mmol), Pd(dppf)Cl$_2$.CH$_2$Cl$_2$ (0.054 g, 0. 07 mmol), and 2M aqueous sodium carbonate solution (3 mL) in 6 mL of tetrahydrofuran to give 0.357 g (34%) of 5-(2-[1-phenylsulfonyl]indolyl)-3-(1-methylpiperidin-4-yl)-1H-indole as an amorphous tan solid, which was dissolved in 25 mL of ethanol, 5 mL of 2N aqueous sodium hydroxide solution and heated, with stirring, at reflux for 2 hours, followed by extractive work-up and silica gel chromatography to give 0.90 g (51%) of the title compound freebase which was dissolved in ethyl acetate and precipitated as its oxalate salt with 1 equivalent of oxalic acid, as an amorphous tan solid. FDMS m/e=329 (M$^+$, free base). EA for $C_{22}H_{23}N_3$ $C_2H_2O_4$: C, 68.72; H, 6.01; N, 10.02. Found: C, 68.45; H, 6.02; N, 9.72.

Example 20

5-(Indol-3-yl)-3-(1-Methylpiperidin-4-yl)-1H-Indole

The title compound was prepared by the procedure of Example 14, beginning with 3-(1-methylpiperidin-4-yl)-1H-indole-5-boronic acid (0.450 g, 1.74 mmol), 3-iodo-1-(phenylsulfonyl)indole (0.636 g, 1.66 mmol), Pd(dppf)Cl$_2$.CH$_2$Cl$_2$ (0.041 g, 0.03 eq, 0.05 mmol), and 2M aqueous sodium carbonate solution (3 mL) in 6 mL of tetrahydrofuran to give 0.508 g (65%) of 5-(3-[1phenylsulfonyl]indolyl)-3-(1-methylpiperidin-4-yl)-1H-indole as an amorphous tan solid, which was dissolved in 30 mL of ethanol, 5 mL of 2N aqueous sodium hydroxide solution and heated, with stirring, at reflux for 2 hours, followed by extractive work-up and silica gel chromatography to give 0.162 g (55%) of the title compound as an amorphous yellow solid. FDMS m/e=329 (M$^+$). EA calculated for $C_{22}H_{23}N_3$: C, 80.21; H, 7.04; N, 12.75. Found: C, 80.50; H, 6.94; N, 12.45.

Example 21

5-(Indazol-3-yl)-3-(1-Methylpiperidin-4-yl)-1H-Indole

The title compound was prepared by the procedure of Example 14, beginning with 3-(1-methylpiperidin-4-yl)-1H- indole-5-boronic acid (0.250 g, 0.97 mmol), 3-chloro-1-(tert-butoxycarbonyl)indazole (0.230 g, 0.92 mmol), Pd(dppf)Cl$_2$ CH$_2$Cl$_2$ (0.023 g, 0.028 mmol), and 2M aqueous sodium carbonate solution (2 mL) in 6 mL of tetrahydrofuran to give 0.197 g (47%) of 5-(3-[1-tert-butoxycarbonyl]indazolyl)-3-(1-methylpiperidin-4-yl)-1H-indole as an amorphous tan solid, which was dissolved in 3 mL of tetrahydrofuran, followed by the addition of sodium methoxide (0.074 g, 1.38 mmol) in 1 mL of methanol, and the mixture was allowed to stir at room temperature for 0.5 hours, followed by extractive work-up and silica gel chromatography to give 0.062 g (54%) of the title compound as an amorphous off-white solid. FDMS m/e=330 (M$^+$). EA calculated for C$_{21}$H$_{22}$N$_4$.½ H$_2$O C, 74.31; H, 6.83; N, 16.50. Found: C, 74.52; H, 6.96; N, 15.95.

Example 22

5-(4-Carboxamidophenyl)-3-(1-Methylpiperidin-4-yl)-1H-Indole

The title compound was prepared by the procedure of Example 10, beginning with 3-(1-methylpiperidin-4-yl)-1H-indole-5-boronic acid (0.200 g, 0.77 mmol), 4-bromobenzamide (0.148 g, 0.74 mmol), tetrakis (triphenylphosphine)palladium(0) (0.045 g, 0.039 mmol), and 2M aqueous sodium carbonate solution (2 mL) in 15 mL of tetrahydrofuran:methanol (1:1) to give the title compound (0.157 g, 64%) as an amorphous solid. FDMS m/e=333 (M$^+$). EA calculated for C$_{21}$H$_{23}$N$_3$O.½ H$_2$O: C, 73.66; H, 7.06; N, 12.27. Found: C, 73.94; H, 6.94; N, 12.15.

Example 23

5-(4-(4-Fluorobenzamido)phenyl)-3-(1-Methylpiperidin-4-yl)-1H-Indole

The title compound was prepared by the procedure of Example 10, beginning with 3-(1-methylpiperidin-4-yl)-1H-indole-5-boronic acid (0.200 g, 0.77 mmol), 1-bromo-4-(4-fluorobenzamido)benzene (0.217 g, 0.74 mmol), tetrakis (triphenylphosphine)palladium(0) (0.045 g, 0.039 mmol), and 2M aqueous sodium carbonate solution (2 mL) in 15 mL of tetrahydrofuran:methanol (1:1) to give the title compound (0.093 g, 29%) as an amorphous solid. FDMS m/e=427 (M$^+$). EA calculated for C$_{27}$H$_{26}$N$_3$OF: C, 75.85; H, 6.13; N, 9.83. Found: C, 75.55; H, 6.18; N, 9.73.

Example 24

5-(4-(Fur-2-ylamido)phenyl)-3-(1-Methylpiperidin-4-yl)-1H-Indole

The title compound was prepared by the procedure of Example 10, beginning with 3-(1-methylpiperidin-4-yl)-1H-indole-5-boronic acid (0.200 g, 0.77 mmol), 1-bromo-4-(2-furylamido)benzene (0.196 g, 0.74 mmol), tetrakis (triphenylphosphine)palladium(0) (0.043 g, 0.037 mmol), and 2M aqueous sodium carbonate solution (2 mL) in 15 mL of tetrahydrofuran:methanol (1:1) to give the title compound (0.109 g, 37%) as an amorphous solid. FDMS m/e=399 (M$^+$). EA calculated for C$_{25}$H$_{25}$N$_3$O.¼ H2O: C, 74.32; H, 6.36; N, 10.40. Found: C, 74.04; H, 6.30; N, 10.10.

Example 25

5-(4-Acetamidophenyl)-3-(1-Methylpiperidin-4-yl)-1H-Indole

The title compound was prepared by the procedure of Example 10, beginning with 3-(1-methylpiperidin-4-yl)-1H-indole-5-boronic acid (0.200 g, 0.77 mmol), 1-bromo-4-acetamidobenzene (0.158 g, 0.74 mmol), tetrakis (triphenylphosphine)palladium(0) (0.045 g, 0.039 mmol), and 2M aqueous sodium carbonate solution (2 mL) in 15 mL of tetrahydrofuran:methanol (1:1) to give the title compound (0.101 g, 40%) as an amorphous solid. FDMS m/e=348 (M$^+$). EA calculated for C$_{22}$H$_{25}$N$_3$O.¼ H$_2$O: C, 75.07; H, 7.16; N, 11.94. Found: C, 74.94; H, 7.00; N, 11.61.

Example 26

5-(4-Acetylphenyl)-3-(1-Methylpiperidin-4-yl)-1H-Indole

The title compound was prepared by the procedure of Example 10, beginning with 3-(1-methylpiperidin-4-yl)-1H-indole-5-boronic acid (0.200 g, 0.77 mmol), 1-bromo-4-acetylbenzene (0.147 g, 0.74 mmol), tetrakis (triphenylphosphine)palladium(O) (0.045 g, 0.039 mmol), and 2M aqueous sodium carbonate solution (2 mL) in 15 mL of tetrahydrofuran:methanol (1:1) to give the title compound (0.171 g, 70%) as an amorphous solid. FDMS m/e=348 (M$^+$). EA calculated for C$_{22}$H$_{24}$N$_2$O.¼ H$_2$O: C, 78.19; H, 7.31; N, 8.29. Found: C, 78.00; H, 7.27; N, 7.93.

Example 27

5-(2-(6-(Fur-2-yl)amido)pyrazinyl)-3-(1-Methylpiperidin-4-yl)-1H-Indole

The title compound was prepared by the procedure of Example 10, beginning with 3-(1-methylpiperidin-4-yl)-1H-indole-5-boronic acid (0.200 g, 0.77 mmol), 2-chloro-6-(2-furylamido)pyrazine (0.163 g, 0.73 mmol), tetrakis (triphenylphosphine)palladium(0) (0.045 g, 0.039 mmol), and 2M aqueous sodium carbonate solution (2 mL) in 15 mL of tetrahydrofuran:methanol (1:1) to give the title compound (0.145 g, 49%) as an amorphous yellow solid. FDMS m/e=401 (M$^+$). EA calculated for C$_{22}$H$_{24}$N$_2$O.½ H$_2$O: C, 67.30; H, 5.89; N, 17.06. Found: C, 67.64; H. 5.97; N, 16.83.

Example 28

5-(4-Aminophenyl)-3-(1-Methylpiperidin-4-yl)-1H-Indole

A solution of 5-(4-acetamido phenyl)-3-(1-methylpiperidin-4-yl)-1H-indole (0.150 g, 0.43 mmol) in 2 mL of ethanol and 1 mL of 1N aqueous hydrochloric acid solution was heated with stirring overnight. The mixture was allowed to cool to room temperature, solvent was removed in vacuo, and the residue was dissolved in 2N aqueous sodium hydroxide solution and ethyl acetate. The organic layer was separated, extracted with 2N aqueous sodium hydroxide solution followed by brine, dried over sodium sulfate, filtered, concentrated and purified by silica gel (flash) chromatography to give the title compound (0.068 g, 52%) as an amorphous yellow solid. FDMS m/e=305 (M$^+$). EA calculated for C$_{20}$H$_{23}$N$_3$: C, 78.65; H, 7.59; N, 13.76. Found: C, 78.42; H, 7.71; N, 13.57.

Example 29

5-(5-Fluorobenzimidazol-2-yl)-3-(1-Methylpiperidin-4-yl)-1H-Indole

A solution of 5-formyl-3-(1-methylpiperidin-4-yl)-1H-indole (0.210 g, 0.90 mmol), and 4-fluoro-o-phenylenediamine (0.112 g, 0.90 mmol), in 15 mL of nitrobenzene was heated, with stirring, at 150–160° C. for 24 hours. An additional 0.5 equivalents of the diamine was added, and heating continued for an additional 24 hours. The solution was allowed to cool to room temperature, the solvent was removed in vacuo, and the residue was purified by silica gel chromatography (dichloromethane:methanol 10:1.5) to give the title compound (0.075 g, 25%) as an amorphous tan solid. FDMS m/e=348 (M⁺). EA calculated for $C_{21}H_{21}N_4F \cdot \frac{3}{4} H_2O$: C, 69.69; H, 6.27; N, 15.48. Found: C, 69.61; H, 6.19; N, 15.17.

Example 30

5-(5-Chlorobenzimidazol-2-yl)-3-(1-Methylpiperidin-4-yl)-1H-Indole

A solution of 5-formyl-3-(1-methylpiperidin-4-yl)-1H-indole (0.210 g, 0.90 mmol), and 4-chloro-o-phenylenediamine (0.197 g, 1.38 mmol), in 15 mL of nitrobenzene was heated, with stirring, at 150–160° C. for 24 hours. The solution was allowed to cool to room temperature, the solvent was removed in vacuo, and the residue was purified by silica gel chromatography (dichloromethane:methanol 10:1.5) to give the title compound (0.215 g, 68%) as an amorphous tan solid. FDMS m/e=365 (M⁺). EA calculated for $C_{21}H_{21}N_4Cl \cdot \frac{1}{4} H_2O$ C, 68.28; H, 5.87; N, 15.17. Found: C, 68.32; H, 6.17; N, 14.51.

The compounds of this invention are useful for increasing activation of the 5-HT$_{1F}$ receptor. An increase in the activation of the 5-HT$_{1F}$ receptor is useful for treating a variety of disorders which have been linked to decreased neurotransmission of serotonin in mammals, e.g., migraine headaches. For further instruction on the nexus between activation of the 5-HT$_{1F}$ and migraine, see the previously incorporated by reference U.S. Pat. No. 5,708,008.

To demonstrate the use of the compounds of this invention in the treatment of migraine, their ability to bind to the 5-HT$_{1F}$ receptor subtype was determined. The ability of the compounds of this invention to bind to the 5-HT$_{1F}$ receptor subtype was measured essentially as described in N. Adham, et al., *Proceedings of the National Academy of Sciences (USA)*, 90:408–412, 1993.

Membrane Preparation: Membranes were prepared from transfected Ltk- cells (transfected with the human 5HT$_{1F}$ receptor sequence) which were grown to 100% confluency. The cells were washed twice with phosphate-buffered saline, scraped from the culture dishes into 5 mL of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford. *Anal. Biochem.*, 72:248–254, 1976.

Radioligand Binding: [³H-5-HT] binding was performed using slight modifications of the 5-HT$_{1D}$ assay conditions reported by Herrick-Davis and Titeler (*J. Neurochem.*, 50:1624–1631, 1988) with the omission of masking ligands. Radioligand binding studies were achieved at 37° C. in a total volume of 250 mL of buffer (50 mM Tris, 10 mM MgCl$_2$, 0.2 mM EDTA, 10 mM pargyline, 0.1% ascorbate, pH=7.4 at 37° C.) in 96 well microtiter plates. Saturation studies were conducted using [³H]5-HT at 12 different concentrations ranging from 0.5 nM to 100 nM. Displacement studies were performed using 4.5–5.5 nM [³H]5-HT. The binding profile of drugs in competition experiments was accomplished using 6–12 concentrations of compound. Incubation times were 30 minutes for both saturation and displacement studies based upon initial investigations which determined equilibrium binding conditions. Nonspecific binding was defined in the presence of 10 mM 5-HT. Binding was initiated by the addition of 50 mL membrane homogenates (10–20 µg). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [³H]5-HT averaged between 45–50%. Binding data was analyzed by computer-assisted nonlinear regression analysis (Accufit and Accucomp, Lunden Software, Chagrin Falls, Ohio). IC50 values were converted to $K_i$ values using the Cheng-Prusoff equation. *Biochem. Pharmacol.*, 22:3099–3108, 1973. All experiments were performed in triplicate. Representative compounds of this invention were found to have affinity for the 5-HT$_{1F}$ receptor as measured by the procedure described above.

As was reported by R. L. Weinshank, et al., WO93/14201, the 5-HT$_{1F}$ receptor is functionally coupled to a G-protein as measured by the ability of serotonin and serotonergic drugs to inhibit forskolin stimulated cAMP production in NIH3T3 cells transfected with the 5-HT$_{1F}$ receptor. Adenylate cyclase activity was determined using standard techniques. A maximal effect is achieved by serotonin. An $E_{max}$ is determined by dividing the inhibition of a test compound by the maximal effect and determining a percent inhibition. N. Adham, et al., supra,; R. L. Weinshank, et al., *Proceedings of the National Academy of Sciences (USA)*, 89:3630–3634, 1992; and the references cited therein.

Measurement of cAMP formation: Human 5HT$_{1F}$ receptor transfected NIH3T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 µM pargyline for 20 minutes at 37° C., 5% CO$_2$. Drug dose-effect curves were then conducted by adding 6 different final concentrations of drug, followed immediately by the addition of forskolin (10 NmM). Subsequently, the cells were incubated for an additional 10 minutes at 37° C., 5% CO$_2$. The medium was aspirated and the reaction was stopped by the addition of 100 mM HCl. To demonstrate competitive antagonism, a dose-response curve for 5-HT was measured in parallel, using a fixed dose of methiothepin (0.32 mM). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software. Representative compounds of the invention shown to have affinity for the 5-HT$_{1F}$ receptor were tested and found to be agonists at the 5-HT$_{1F}$ receptor in the cAMP assay.

The type of formulation employed for the administration of the compounds employed in the methods of the present invention may be dictated by the particular compounds employed, the type of pharmacokinetic profile desired from the route of administration and the compound(s), and the state of the patient.

Formulations amenable to oral or injectable administration are prepared in a manner well known in the pharmaceutical art and comprise at least one active compound. See, e.g., REMINGTON'S PHARMACEUTICAL SCIENCES, (16th ed. 1980).

In general, a formulation of the present invention includes an active ingredient (a compound of formula I) and is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compounds of the invention can be formulated so as to provide quick, sustained or delayed release of the active ingredient after administration to the patient by employing procedures known in the art.

The following formulation examples are illustrative only and are not intended to limit the scope of the present invention. The term "active ingredient" refers to a compound of formula I.

Formulation Example 1

Hard Gelatin Capsules

| Ingredient | Quantity (mg/capsule) |
| --- | --- |
| Active ingredient | 30.0 |
| Starch | 305.0 |
| Magnesium stearate | 5.0 |

The above ingredients are mixed and filled into hard gelatin capsules in 340 mg quantities.

Formulation Example 2

Tablet

| Ingredient | Quantity (mg/tablet) |
| --- | --- |
| Active ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

Dry Powder Inhaler

| Ingredient | Weight % |
| --- | --- |
| Active ingredient | 5 |
| Lactose | 95 |

The active ingredient is mixed with the lactose and the mixture is added to a dry powder inhaling appliance.

Formulation Example 4

Tablet

| Ingredient | Quantity (mg/tablet) |
| --- | --- |
| Active ingredient | 30.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C.–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules

| Ingredient | Quantity (mg/capsule) |
| --- | --- |
| Active ingredient | 40.0 |
| Starch | 109.0 |
| Magnesium stearate | 1.0 |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories

| Ingredient | Amount |
| --- | --- |
| Active ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat Fg. necessary. The mixture is then poured into a suppository mold of nominal 2.0 g capacity and allowed to cool.

Formulation Example 7

Suspensions

| Ingredient | Amount |
| --- | --- |
| Active ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules

| Ingredient | Quantity (mg/capsule) |
| --- | --- |
| Active ingredient | 15.0 |
| Starch | 407.0 |
| Magnesium stearate | 3.0 |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

Intravenous Formulation

| Ingredient | Quantity |
| --- | --- |
| Active ingredient | 250.0 mg |
| Isotonic saline | 1000 ml |

Formulation Example 10

Topical Formulation

| Ingredient | Quantity |
| --- | --- |
| Active ingredient | 1–10 g |
| Emulsifying wax | 30 g |
| Liquid paraffin | 20 g |
| White soft paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or Buccal Tablets

| Ingredient | Quantity (mg/tablet) |
| --- | --- |
| Active ingredient | 10.0 |
| Glycerol | 210.5 |
| Water | 143.0 |
| Sodium citrate | 4.5 |
| Polyvinyl alcohol | 26.5 |
| Polyvinylpyrrolidone | 15.5 |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the active ingredient is slowly admixed. The homogenous mixture is poured into forms made of an inert material to produce a drug-containing diffusion matrix having a thickness of about 2–4 mm. This diffusion matrix is then cut to form individual tablets having the appropriate size.

While it is possible to administer a compound employed in the methods of this invention directly without any formulation, the compounds are usually administered in the form of pharmaceutical compositions comprising a pharmaceutical excipient and at least one active ingredient. These formulations can be administered by a variety of routes including oral, buccal, rectal, intranasal, transdermal, subcutaneous, intravenous, intramuscular, and intranasal. Many of the compounds employed in the methods of this invention are effective as both injectable and oral compositions.

In order to administer transdermally, a transdermal delivery device ("patch") is needed. Such transdermal patches may be used to provide continuous or discontinuous infusion of a compound of the present invention in controlled amounts. The construction and use of transdermal patches for the delivery of pharmaceutical agents is well known in the art. See, e.g., U.S. Pat. No. 5,023,252, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, which is herein incorporated by reference. The delivery of hydrophilic drugs may be enhanced by intra-arterial infusion of hypertonic solutions which can transiently open the blood-brain barrier.

A compound of formula I is preferably formulated in a unit dosage form, each dosage containing from about 0.001 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient as described above.

The active compounds are generally effective over a wide dosage range. For examples, dosages per day normally fall within the range of about 0.0001 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

We claim:

1. A compound of formula I:

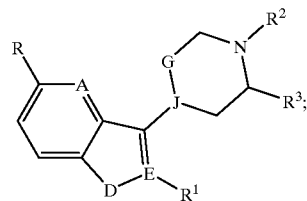

or a pharmaceutical acid addition salt thereof; where:

A is nitrogen;

D is NH;

E is carbon;

G—J is $CH_2$—CH or CH=C;

R is phenyl, substituted phenyl, naphthyl, substituted naphthyl, heteroaryl, or substituted heteroaryl;

$R^1$ is hydrogen or $C_1$–$C_6$ alkyl;

$R^2$ is hydrogen or $C_1$–$C_6$ alkyl;

$R^3$ is hydrogen or $R^2$ and $R^3$ combine, together with the 6 membered ring to which they are attached, to form a 6:5, 6:6, or 6:7 fused bicyclic ring.

2. The compound of claim 1 where G—J is $CH_2$—CH, $R^1$ is hydrogen, and $R^2$ is $C_1$–$C_4$ alkyl; or a pharmaceutical acid addition salt thereof.

3. The compound of claim 2 where R is a naphthyl or phenyl group and the phenyl or naphthyl group is optionally substituted once with halo, $C_1$–$C_4$ alkyl, $C_1$–$C_4$ alkoxy, amino, carboxamido, NHC(O)-heteroaryl, NHC(O)-substituted heteroaryl, acetyl, or trifluoromethyl and $R^2$ is methyl; or a pharmaceutical acid addition salt thereof.

4. The compound of claim 3 where the phenyl or naphthyl group is substituted once with amino, fluoro, chloro, methyl, carboxamido, acetyl, trifluoromethyl, or methoxy; or a pharmaceutical acid addition salt thereof.

5. The compound of claim 2 where R is a heteroaryl group selected from: thienyl, quinolinyl, benzimidazolyl, benzothiophenyl, thiazolyl, benzothiazolyl, indolyl, and indazolyl where the heteroaryl group is optionally a substituted once with halo, $C_1$–$C_4$ alkyl, $C_1$–$C_4$ alkoxy, a mino, carboxamido, NHC(O)-heteroaryl, and trifluoromethyl; and $R^2$ is methyl; or a pharmaceutical acid addition salt thereof.

6. The compound of claim 5 where the optionally substituted heteroaryl group is unsubstituted; or a pharmaceutical acid addition salt thereof.

7. A pharmaceutical formulation comprising a compound of formula I:

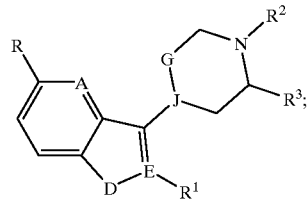

or a pharmaceutical acid addition salt thereof; where:

A is nitrogen or carbon;
D is oxygen, sulfur, or NH;
E is carbon or nitrogen;
G—J is $CH_2$—CH or CH=C;
R is phenyl, substituted phenyl, naphthyl, substituted naphthyl, heteroaryl, or substituted heteroaryl;
$R^1$ is hydrogen or $C_1$–$C_6$ alkyl;
$R^2$ is hydrogen or $C_1$–$C_6$ alkyl;
$R^3$ is hydrogen or $R^2$ and $R^3$ combine, together with the 6 membered ring to which they are attached, to form a 6:5, 6:6, or 6:7 fused bicyclic ring.

8. A method for activating 5-$HT_{1F}$ receptors in a mammal comprising administering to a mammal in need of such activation an effective amount of a compound of formula I:

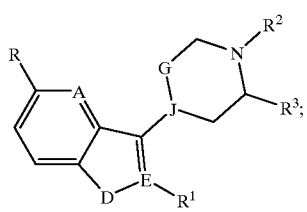

I or a pharmaceutical acid addition salt thereof; where:
A is nitrogen or carbon;
D is oxygen, sulfur, or NH;
E is carbon or nitrogen;
G—J is $CH_2$—CH or CH=C;
R is phenyl, substituted phenyl, naphthyl, substituted naphthyl, heteroaryl, or substituted heteroaryl;
$R^1$ is hydrogen or $C_1$–$C_6$ alkyl;
$R^2$ is hydrogen or $C_1$–$C_6$ alkyl;
$R^3$ is hydrogen or $R^2$ and $R^3$ combine, together with the 6 membered ring to which they are attached, to form a 6:5, 6:6, or 6:7 fused bicyclic ring.

9. The method according to claim 8 where the mammal is a human.

10. A method for inhibiting neuronal protein extravasation in a mammal comprising administering to a mammal in need of such inhibition an effective amount of a compound of formula I:

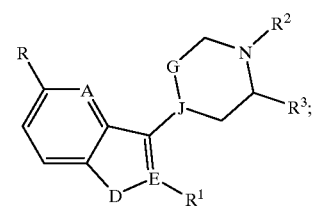

I or a pharmaceutical acid addition salt thereof; where:
A is nitrogen or carbon;
D is oxygen, sulfur, or NH;
E is carbon or nitrogen;
G—J is $CH_2$—CH or CH=C;
R is phenyl, substituted phenyl, naphthyl, substituted naphthyl, heteroaryl, or substituted heteroaryl;
$R^1$ is hydrogen or $C_1$–$C_6$ alkyl;
$R^2$ is hydrogen or $C_1$–$C_6$ alkyl;
$R^3$ is hydrogen or $R^2$ and $R^3$ combine, together with the 6 membered ring to which they are attached, to form a 6:5, 6:6, or 6:7 fused bicyclic ring.

11. The method according to claim 10 where the mammal is a human.

* * * * *